US009937265B2

(12) United States Patent
Ingham et al.

(10) Patent No.: US 9,937,265 B2
(45) Date of Patent: Apr. 10, 2018

(54) SELF-ASSEMBLING PEPTIDE AND POLYSACCHARIDE COMPLEXES

(71) Applicant: University of Leeds, Leeds (GB)

(72) Inventors: Eileen Ingham, Leeds (GB); Ruth Karen Wilcox, Leeds (GB); Amalia Aggeli, Thessaloniki (GR); Danielle Elizabeth Miles, Leeds (GB)

(73) Assignee: University of Leeds, Leeds (GB)

( * ) Notice: Subject to any disclaimer, the term of this patent is extended or adjusted under 35 U.S.C. 154(b) by 0 days.

(21) Appl. No.: 14/782,961

(22) PCT Filed: Apr. 8, 2014

(86) PCT No.: PCT/GB2014/051090
§ 371 (c)(1),
(2) Date: Oct. 7, 2015

(87) PCT Pub. No.: WO2014/167310
PCT Pub. Date: Oct. 16, 2014

(65) Prior Publication Data
US 2016/0058871 A1 Mar. 3, 2016

(30) Foreign Application Priority Data
Apr. 8, 2013 (GB) .................................. 1306338.3

(51) Int. Cl.
| | |
|---|---|
| *A61K 38/08* | (2006.01) |
| *A61K 47/48* | (2006.01) |
| *A61K 9/00* | (2006.01) |
| *A61K 31/726* | (2006.01) |
| *A61K 38/04* | (2006.01) |
| *A61K 31/728* | (2006.01) |
| *C08L 5/08* | (2006.01) |
| *C07K 7/06* | (2006.01) |
| *C08L 5/02* | (2006.01) |
| *A61M 5/19* | (2006.01) |

(52) U.S. Cl.
CPC .......... *A61K 47/481* (2013.01); *A61K 9/0019* (2013.01); *A61K 9/0024* (2013.01); *A61K 31/726* (2013.01); *A61K 31/728* (2013.01); *A61K 38/04* (2013.01); *A61K 38/08* (2013.01); *A61K 47/48784* (2013.01); *A61M 5/19* (2013.01); *C07K 7/06* (2013.01); *C08L 5/02* (2013.01); *C08L 5/08* (2013.01)

(58) Field of Classification Search
CPC .. A61K 2300/00; A61K 31/728; A61K 38/04; A61K 31/726; A61K 38/08; A61K 47/481; A61K 47/48784; A61K 9/0019; A61K 9/0024; A61M 5/19; C07K 7/06; C08L 5/02; C08L 5/08
USPC ........................ 514/16.7, 20.9; 530/322, 327
See application file for complete search history.

(56) References Cited

U.S. PATENT DOCUMENTS

| | | | |
|---|---|---|---|
| 6,034,211 A | 3/2000 | Kelly | |
| 7,101,990 B2 | 9/2006 | Contreras | |
| 7,678,883 B2 | 3/2010 | Cheng et al. | |
| 7,700,721 B2 | 4/2010 | Boden et al. | |
| 8,586,539 B2 | 11/2013 | Boden et al. | |
| 9,062,312 B2 | 6/2015 | Rouviere et al. | |
| 9,101,687 B2 | 8/2015 | Boden et al. | |
| 9,187,527 B2 | 11/2015 | Boden et al. | |
| 9,193,764 B2 | 11/2015 | Boden et al. | |
| 9,315,550 B2 | 4/2016 | Boden et al. | |
| 2003/0162696 A1 | 8/2003 | Mihara | |
| 2005/0181985 A1* | 8/2005 | Hemberger | A61K 47/4823 424/85.2 |
| 2006/0154852 A1 | 7/2006 | Boden et al. | |
| 2007/0277250 A1* | 11/2007 | Stupp | A61K 38/08 800/9 |
| 2007/0292514 A1 | 12/2007 | Chan Pui et al. | |
| 2010/0040879 A1 | 2/2010 | Koopmans et al. | |
| 2010/0040880 A1 | 2/2010 | Koopmans et al. | |
| 2010/0234304 A1 | 9/2010 | Boden et al. | |
| 2013/0012457 A1 | 1/2013 | Boden et al. | |
| 2014/0044649 A1 | 2/2014 | Boden et al. | |

(Continued)

FOREIGN PATENT DOCUMENTS

| | | |
|---|---|---|
| EP | 1935438 A1 | 6/2008 |
| WO | WO 03/006494 A1 | 1/2003 |

(Continued)

OTHER PUBLICATIONS

Protopapa et al, "Interaction of self-assembling beta-sheet peptides with phospholipid monolayers: The effect of serine, threonine, glutamine and asparagine amino acid side chains," Electrochimica Acta, available online Jan. 14, 2010, 3368-3375.*
Aggeli et al., "Self-assembling peptide polyelectrolyte β-sheet complexes form nematic hydrogels," *Angewandte Chemie International Edition*, vol. 42, pp. 5603-5606, 2003.
Carrick et al., "Effect of ionic strength on the self-assembly, morphology and gelation of pH responsive β-sheet tape-forming peptides," *Tetrahedron*, vol. 63, pp. 7457-7467, 2007.
EPSRC Details of Grant, EPSRC Reference No. EP/D070791/1, "Self assembly of GAG-functionalised peptides into proteoglycan-like molecules for tissue engineering," http://gow.epsrc.ac.uk/NGBOViewGrant.aspx?-GrantRef=EP/D070791/1, Jan. 15, 2007-Jul. 14, 2010.
International Search Report and Written Opinion for PCT/GB2014/051090 dated Jun. 25, 2014 (11 pages).

(Continued)

Primary Examiner — Julie Ha
(74) Attorney, Agent, or Firm — Klarquist Sparkman, LLP

(57) ABSTRACT

Novel self-assembling peptide complexes comprising a charged peptide and a polysaccharide, methods of producing them and uses therefore are described. The novel self-assembling peptide complexes have particular utility in the restoration of biomechanical or biochemical function of a variety of biological tissues, for example and without limitation, in degenerated spinal discs, osteoarthritic joints, damaged cartilage, meniscus, ligaments, tendons, dental, ophthalmic and cardiovascular and blood vessel tissues. Methods of repairing and or restoring biomechanical or biochemical function of biological tissues and scaffolds for the support of cell growth are also described.

25 Claims, 7 Drawing Sheets

(56) References Cited

U.S. PATENT DOCUMENTS

| | | |
|---|---|---|
| 2014/0186313 A1 | 7/2014 | Boden et al. |
| 2015/0299266 A1 | 10/2015 | Boden et al. |
| 2016/0046670 A1 | 2/2016 | Boden et al. |
| 2016/0185824 A1 | 6/2016 | Boden et al. |
| 2016/0199283 A1 | 7/2016 | Hug et al. |
| 2016/0340392 A1 | 11/2016 | Boden et al. |

FOREIGN PATENT DOCUMENTS

| | | | |
|---|---|---|---|
| WO | WO 2004/007532 A2 | 1/2004 | |
| WO | WO 2004/069296 A1 | 8/2004 | |
| WO | WO 2006/096614 A2 | 9/2006 | |
| WO | WO 2007/148334 A1 | 12/2007 | |
| WO | WO 2008/078157 A2 | 7/2008 | |

OTHER PUBLICATIONS

Riley et al., "Bioproduction and characterization of a pH responsive self-assembling peptide," *Biotechnology & Bioengineering*, vol. 103 (2), pp. 241-251, Jun. 1, 2009.

Search Report from the British Intellectual Property Office (UKIPO) for GB1306338.3 dated Jan. 30, 2014 (5 pages).

Aggeli et al., "Responsive Gels Formed by the Spontaneous Self-Assembly of Peptides Into Polymeric β-Sheet Tapes," *Nature* 386:259-262, 1997.

Aggeli et al., "Self-Assembling Homopolymeric Peptide Tapes in Aqueous Solution," Peptide Science—Present and Future (eds.), pp. 30-33, 1999.

Aggeli et al., "Structure and Dynamic of Self-Assembing β-Sheet Peptide Tapes by Dynamic Light Scattering," *Biomacromolecules* 2:378-388, 2001.

Aggeli et al., "pH as a Trigger of Peptide β-Sheet Self-Assembly and Reversible Switching between Nematic and Isotropic Phases," *J Am Chem Soc. 125*:9619-9628, 2003.

Bell et al., "Self-Assembling Peptides as Injectable Lubricants for Osteoarthritis," *J Biomedical Materials Res. Part A*, pp. 235-246, Apr. 2006.

biowww.net/buffer-reagent/1x-Phosphate-Buffered-Saline.html (printed Mar. 22, 2010).

Credentist Ag, "Regenerating Teeth" from Credentis Innovation Brochure, credentis.com, printed on/or after 2012, Accessed Jun. 1, 2015.

Fishwick et al., "Structures of Helical β-Tapes and Twisted Ribbons: The Role of Side-Chain Interactions on Twist and Bend Behavior," *Nano Lett. 3*:1475-1479, 2003.

Fukushima, "Self-Induced Helix-Sheet Conformational Transitions of an Amphiphilic Peptide," *Polym J. 27*:819-830, 1995.

Kyle et al., "Recombinant Self-Assembling Peptide as Biomaterials for Tissue Engineering," *Biomaterials 31*:9395-9405, 2010.

Nyrkova et al., "Fibril Stability in Solutions of Twisted β-Sheet Peptides: A New Kind of Micellization in Chiral Systems," *Eur Phys J. 17*:481-497, 2000.

Nyrkova et al., "Self-Assembly and Structure Transformations in Living Polymers Forming Fibrils," *Eur Phys J. 17*:499-513, 2000.

Zelezetsky and Tossi, "Alpha-Helical Antimicrobial Peptides—Using a Sequence Template to Guide Structure-Activity Relationship Studies," *Biochim Biophys. Acta 1758*:1436-1449, 2006.

Breyer, "What's in Toothpaste," http://www.mnn.com/health/fitness-well-being/stories/whats-in-toothpaste, March 15, 2012, accessed from the internet Mar. 15, 2017.

Choice, "Want a million-dollar smile without all the marketing?," https://www.choice.com.au/health-and-body/dentist-and-dental-care/dental-products/articles/toothpaste-whats-the-difference, accessed from the internet Mar. 15, 2017.

Colgate-Palmolive Company, Colgate Total® Toothpaste Ingredients, http://www.colgatetotal.com/health-benefits/toothpaste-ingredients, last updated Jul. 24, 2014, accessed from the internet Mar. 15, 2017.

Curodont Protect Product Label, first distributed by Credentist AG on Apr. 3, 2013.

Dental Health Foundation, "What is in Toothpaste?" http://www.dentalhealth.ie/dentalhealth/teeth/toothpaste.html, accessed from the internet Mar. 15, 2017.

Dow Chemical Company, "Carboxymethylcellulose," http://www.dow.com/dowwolff/en/industrial_solutions/polymers/carboxymethylcellulose/, accessed from the internet Mar. 15, 2017.

Food and Drug Administration, "Select Committee on GRAS Substances (SCOGS) Opinion: Carboxymethyl cellulose (packaging) and Sodium carboxymethyl cellulose," http://www.fda.gov/Food/IngredientsPackagingLabeling/GRAS/SCOGS/ucm261244.htm, accessed from the internet Mar. 15, 2017.

Procter & Gamble, Crest Pro Health Toothpastes http://www.pg.com/productsafety/ingredients/Crest_Pro-Health_Toothpaste.pdf, accessed from the internet Mar. 15, 2017.

Qingdao Unionchem Co.,Ltd., "Sodium Carboxymethyl Cellulose (CMC)—Toothpaste Grade," https://www.ulprospector.com/en/eu/PersonalCare/Detail/11065/533195/Sodium-Carboxymethyl-Cellulose-CMC-Toothpaste-Grade, accessed from the internet Mar. 15, 2017.

Sidley Chemical Co., Ltd., "Sodium Carboxymethyl Cellulose (CMC)," http://celluloseether.com/sodium-carboxymethyl-cellulose-cmc/, accessed from the internet Mar. 15, 2017.

Sidley Chemical Co., Ltd., "Thickener in Toothpaste—Sodium Carboxymethyl cellulose," http://celluloseether.com/thickener-in-toothpaste-sodium-carboxymethyl-cellulose/, Jan. 2016, accessed from the internet Mar. 15, 2017.

Sinocmc Co., Ltd., "The application of Sodium Carboxymethyl Cellulose (CMC) in the toothpaste industry," http://www.sino-cmc.com/html_news/Sodium-Carboxymethyl-Cellulose-toothpaste-7.html, Aug. 2, 2012, accessed from the internet Mar. 15, 2017.

Stookey, "Toothpaste—What's In It?" http://www.deardoctor.com/articles/toothpaste-whats-in-it/, accessed from the internet Mar. 15, 2017.

Wikipedia, "Carboxymethyl Cellulose," https://en.wikipedia.org/wiki/Carboxymethyl_cellulose, accessed from the internet Mar. 15, 2017.

\* cited by examiner

SELF-ASSEMBLING PEPTIDE AND POLYSACCHARIDE COMPLEXES

CROSS REFERENCE TO RELATED APPLICATIONS

This is the U.S. National Stage of International Application No. PCT/GB2014/051090, filed Apr. 8, 2014, which was published in English under PCT Article 21(2), which in turn claims the benefit of GB1306338.3, filed Apr. 8, 2013.

The invention relates to novel self-assembling peptide complexes, methods of producing them and uses therefor. The novel self-assembling peptide complexes of the present invention have particular utility in the restoration of biomechanical or biochemical function of a variety of biological tissues, for example and without limitation, in degenerated spinal discs, osteoarthritic joints, damaged cartilage, meniscus, ligaments, tendons, dental, ophthalmic and cardiovascular and blood vessel tissues. The invention provides inter alia methods of repairing and or restoring biomechanical or biochemical function of biological tissues and scaffolds for the support of cell growth.

BACKGROUND

Glycosaminoglycans (GAGs) form an important component of connective tissues, and may be covalently linked to proteins to form proteoglycans, which can act to lubricate interfaces and facilitate relative tissue movement whilst also fulfilling important biological functions. The net negative charge of GAG attracts cations, which in turn attract water molecules. This water is critical to the biomechanical performance of tissues such as the cartilaginous joints and intervertebral discs.

The intervertebral disc is a complex hierarchical structure composed of the annulus fibrosus and nucleus pulposus, which are attached to the vertebral bodies via cartilagenous endplates. The main proteoglycan of the healthy disc is aggrecan, which comprises of a core protein with up to 100 highly sulphated GAG chains (mainly chondroitin and keratan sulphate) covalently attached. The osmotic pressure provided by the sulphated side chains of aggrecan is thought to be responsible for maintaining tissue hydration, which helps to maintain disc height and turgor against high compressive loads. This osmotic pressure is due to the greatly sulphated GAG groups providing a highly fixed negative charge on the matrix. This in turn attracts positively charged molecules such as small cations into the tissue to balance the negative charges. The osmotic response action of the disc is also thought to be important for nutrient and metabolite transport.

Back pain affects a large proportion of the population, with 80% of adults experiencing an episode of back pain during their lifetimes, resulting in a wide range of effects from mild discomfort to complete immobilisation. Back pain is the most common reason given for days off work and it is estimated that the total cost including lost working hours, benefits and healthcare is between 1 and 2% of the gross national product in Western European countries. Lower back pain is strongly associated with degeneration of the intervertebral discs. During degeneration, the aggrecan molecules degrade and the smaller fragments leach from the tissue more readily than the larger portions, which in turn results in a loss of GAGs. The nucleus becomes more fibrotic and less gel-like and there is a loss in disc height, affecting the mechanics of the rest of the spinal column.

Current surgical interventions for low back pain such as spinal fusions and total disc replacements are highly invasive surgical interventions and have relatively poor long term success rates. Therefore, in recent years there has been an interest in developing new therapies to address disc degeneration, such as transplantation, regeneration, repair and replacement. In particular in order to maintain motion in the spinal segment, the replacement of the nucleus without annular obliteration represents a tempting alternative to spinal fusion and total disc replacement procedures.

Considerable effort has been put into tissue engineered approaches to nucleus augmentation. The disc is the largest avascular tissue in the body and therefore has a hostile environment of low pH, low glucose and oxygen levels and high lactate levels. Therefore, a major challenge with tissue engineered approaches is to successfully maintain cell viability. An alternative to cell based therapies is to replace the tissue with a synthetic equivalent.

The aims in any nucleus pulposus replacement are to restore normal load distribution to the diseased level and restore segmental spinal mechanics. In order to be a successful an ideal nucleus replacement device should be: biocompatible without significant systemic or local reactions of toxicity, be stable under varying physiological loading and environmental conditions, be capable of restoring disc height and osmotic pressures and be similar in stiffness to the native tissue. In addition an ideal nucleus replacement device should be implanted using minimally invasive procedures, which limit the destruction of the surrounding tissue, for example, a hydrogel that forms in situ and is injected through a narrow gauge needle as a mobile fluid.

It is known from the prior art (WO 2004/007532) that β-sheet tape forming peptides, which self-assemble in one dimension into a hierarchy of well defined structures, are useful in a variety of biomedical areas. Self-assembling peptides can form long chains and complex structures, which can mimic collagen. These gel forming peptides are advantageous as biomaterials as they are based on entirely natural amino acids, they are highly versatile since they can be made to be either positively or negatively charged, polar or amphiphilic or based on different types of polar uncharged amino acids, and also that the self-assembly can be triggered by external environment such as pH, ionic strength and temperature. Reconstruction of the nucleus pulposus, whilst preserving the biomechanics of the annulus fibrosus and cartilage endplates would offer immediate advantages to patients and clinicians alike.

A nucleus pulposus replacement that can form a stable hydrogel and mimic the mechanical function of natural tissue and that provides a charged environment that will lead to the restoration of the disc swelling pressure would offer immediate advantages to patients and clinicians alike.

A nucleus pulposus replacement that can be injectable and thus minimally invasive would offer immediate advantages to patients and clinicians alike.

An injectable minimally invasive agent that could be used as an early intervention to prevent progression of disc tissue degeneration would offer immediate advantages to patients and clinicians alike.

BRIEF SUMMARY OF THE DISCLOSURE

According to a first aspect of the invention there is provided a composition of matter comprising a self-assembling peptide complex comprising:

(i) at least one charged peptide capable of self-assembling; and
(ii) an oppositely or same charged polysaccharide.

In one embodiment of the invention, the peptide capable of one self-assembling has an overall net positive charge and more preferably has an overall net even number charge of for example +2, +4 or +6.

Preferably, the peptide capable of self-assembling is selected from the group P11-12 (SEQ ID NO:2), P11-8 (SEQ ID NO:1), P11-14 (SEQ ID NO:3), P11-16 (SEQ ID NO:4), P11-18 (SEQ ID NO:5), P11-19 (SEQ ID NO; 6), P11-26 (SEQ ID NO; 7), P11-28 (SEQ ID NO:8), P11-31 (SEQ ID NO:9) and P11-32 (SEQ ID NO:10).

The positively charged peptides capable of self-assembling (SAPs) of the present inventions are preferably 11 residues in length, and as mentioned hereinbefore the SAPs share the commonality of possessing an overall net positive charge of at least +2. The positively charged SAPs of the present invention also share sequence homology.

Preferably, the amino acid residues in positions 5 and 7 are ornithine (O).

Preferably, the amino acid residues at positions 1 and 2 are the same but reversed at positions 10 and 11.

Preferably, the amino acid residues at positions 1 and 2 are the same and are selected from the group comprising serine (SS), glutamine (QQ), threonine (TT) and asparagine (NN). In one embodiment of the invention where the SAP is the SAP P11-28 the amino acid residues at positions 1 and 2 comprise residues OQ at the terminal positions. In one embodiment of the invention where the SAP is the SAP P11-32 the amino acid residues at positions 1 and 2 comprise residues OS at the terminal positions.

Preferably, the amino acid residues at positions 10 and 11 are the same and are selected from the group comprising serine (SS), glutamine (QQ), threonine (TT) and asparagine (NN), the SAP P11-28 comprises residues QO at the terminal position (the reverse of positions 1 and 2) and the SAP P11-32 comprises residues SO at the terminal position (the reverse of positions 1 and 2).

In some embodiments, the amino acid residues at positions 1 and 2 and 10 and 11 are the same so that they are all either serine (SS), glutamine (QQ), threonine (TT) or asparagine (NN).

Preferably, the amino acid residue at position 3 is either ornithine (O) or arginine (R).

Preferably, the amino acid residue at position 4 is either phenylalanine (F) or glutamine (Q).

Preferably, the amino acid residue at position 6 is either tryptophan (W) or glutamine (Q).

Preferably, the amino acid residue at position 8 is either phenylalanine (F) or glutamine (Q).

Preferably, the amino acid residue at position 9 is either glutamic acid (E) or glutamine (Q).

Also provided is a positively charged SAP wherein the amino acid chain is extended to include a bioactive peptide sequence, or wherein the amino acid chain is attached to a therapeutically active molecule or drug or the like.

Preferably, the polysaccharide is selected from the group comprising glycosaminoglycan, oligosaccharide, mucopolysaccharide and dextran. Preferably, the positively charged peptides capable of self-assembling is complexed with an oppositely charged polysaccharide (negatively charged polysaccharide). In one particular embodiment the negatively charged polysaccharide is a glycosaminoglycan (GAG) and is selected from the group comprising chondroitin sulphates (CS), dermatan sulphates, keratan sulphates, hyaluronan, hyaluronic acid, heparin and heparan sulphate or derivatives thereof.

The polysaccharide may be natural or synthetic. The peptide complex may be selected from a SAP:polysaccharide combination, a SAP:oligosaccharide combination and a SAP:GAG combination. In particular, the peptide complex is a SAP:GAG combination.

In an alternative embodiment, the peptide capable of self-assembling is positively charged peptide and is associated with a polysaccharide selected from the group comprising glycosaminoglycan (GAG), oligosaccharide, mucopolysaccharide and dextran.

Throughout this application a self-assembling peptide complex comprising charged peptides capable of self-assembling and charged polysaccharide may be referred to as a peptide:glycan or a SAP:GAG or a SAP:polysaccharide, a peptide capable of self-assembling may be referred to as a SAP, and a glycosaminoglycan may be referred to as a GAG.

In one embodiment of the invention the self-assembling peptide complex comprises a positively charged SAP: GAG selected from the group comprising P11-12 (SEQ ID NO: 2): GAG, P11-8 (SEQ ID NO: 1): GAG, P11-14 (SEQ ID NO: 3): GAG, P11-16 (SEQ ID NO: 4): GAG, P11-18 (SEQ ID NO: 5): GAG, P11-19 (SEQ ID NO: 6): GAG, P11-26 (SEQ ID NO: 7): GAG, P11-28 (SEQ ID NO: 8):GAG, P11-31 (SEQ ID NO: 9): GAG and P11-32 (SEQ ID NO:10):GAG.

In an alternative embodiment of the invention the peptide capable of one self-assembling has an overall net negative charge and more preferably has an overall even number net charge of for example −2, −4 or −6.

Preferably, the peptide capable of self-assembly is selected from the group P11-4 (SEQ ID NO:11), P11-9 (SEQ ID NO:12), P11-13 (SEQ ID NO:13), P11-15 (SEQ ID NO:14), P11-17 (SEQ ID NO:15), P11-20 (SEQ ID NO; 16), P11-24 (SEQ ID NO; 17), P11-25 (SEQ ID NO:18), P11-27 (SEQ ID NO:19), P11-29 (SEQ ID NO:20) and P11-30 (SEQ ID NO:21).

The negatively charged peptides capable of self-assembling (SAPs) of the present inventions are preferably 11 residues in length, and as mentioned hereinbefore the SAPs share the commonality of possessing an overall net negative charge of at least −2. The negatively charged SAPs of the present invention also share sequence homology.

Preferably, the amino acid residues at positions 5, 7 and 9 are glutamic acid (E).

Preferably, the amino acid residue at position 3 is either glutamic acid (E) or arginine (R).

Preferably, the amino acid residue at positions 4 and 8 are the same and are preferably selected from the group consisting of phenylalanine (F), glutamine (Q) and serine (S).

Preferably, the amino acid residue at position 6 is selected from the group consisting of tryptophan (W), glutamine (Q) and serine (S).

Preferably, the amino acid residues at positions 1 and 2 may be the same or different and reversed at positions 10 and 11.

Preferably, the amino acid residues at positions 1 and 2 are the same and are selected from the group comprising serine (SS), glutamine (QQ), threonine (TT) and asparagine (NN). In one embodiment of the invention where the SAP is the SAP P11-27 the amino acid residues at positions 1 and 2 comprise residues EQ at the terminal positions. In one embodiment of the invention where the SAP is the SAP P11-30 the amino acid residues at positions 1 and 2 comprise residues ES at the terminal positions.

Preferably, the amino acid residues at positions 10 and 11 are the same and are selected from the group comprising serine (SS), glutamine (QQ), threonine (TT) and asparagines (NN), the SAP P11-27 comprises residues QE at the terminal positions (the reverse of positions 1 and 2) and the SAP P11-30 comprises residues SE at the terminal positions (the reverse of positions 1 and 2).

In one embodiment of the invention the self-assembling peptide complex comprises a negatively charged SAP: GAG selected from the group comprising P11-4 (SEQ ID NO: 11): GAG, P11-9 (SEQ ID NO: 12): GAG, P11-13 (SEQ ID NO: 13): GAG, P11-15 (SEQ ID NO: 14): GAG, P11-17 (SEQ ID NO: 15): GAG, P11-20 (SEQ ID NO: 16): GAG, P11-24 (SEQ ID NO: 17): GAG, P11-25 (SEQ ID NO: 18) GAG, P11-27 (SEQ ID NO: 19): GAG, P11-29 (SEQ ID NO:20): GAG and P11-30 (SEQ ID NO:21):GAG.

In some embodiments where the negatively charged peptides capable of self-assembling are used it may be desired to use a positively charged polysaccharide such as chitosan and its derivatives or other cationic polysaccharides. Alternatively, where the complex comprises the positively charged peptides capable of self assembling it may be desired to use a positively charged polysaccharide (i.e of the same charge) such as chitosan and its derivatives or other cationic polysaccharides.

Preferably, the self-assembling peptide complexes of the present invention have an elastic modulus in the range of 1 to 400,000 Pa.

The ratio of peptide to GAG in the complexes is selected according to the required mechanical properties and also the viscosity required.

Preferably, the composition of matter forms a gel or gel like substance within seconds to minutes to days of when the peptide and GAG are mixed. Results presented hereinafter suggest that GAG acts as a trigger for gel formation of the complex and the peptides capable of self-assembling.

It will be appreciated that the mechanical properties of the self-assembling peptide complexes of the present invention can be selected according to a user's requirements. In some applications it may be desirable to provide a gel with a high stiffness value and in other instances the gel may be required to have a lower stiffness value.

Also provided is a charged SAP wherein the amino acid chain is extended to include a bioactive peptide sequence, or wherein the amino acid chain is attached to a therapeutically active molecule or drug or the like.

G' values are associated with a measurement of how solid a material is, whereas G" values are associated with a measurement of the liquid component of a gel. Accordingly it will be appreciated that G' and G" values are an indication of stiffness and the composition of matter comprising a self-assembling peptide complex of the present invention and the values may be selected according to the desired application. For example, in the instance of using the composition of matter for cartilage repair the composition of matter is required to have high mechanical properties and greater stiffness than the mechanical properties required for nucleus pulposus replacement. The G' and G" values for the human nucleus pulposus are 10 kPa and 4.5 kPa respectively, accordingly G' and G" values of the composition of matter comprising a self-assembling peptide complex of the present invention is selected in each instance to be as close to the natural tissue as possible.

Preferably, the self-assembling peptide complexes have a phase angle preferably in the region of 0 to 60° and more preferably still in the region of 5 to 30°. Phase angle is a measure of how solid/liquid-like a material is, a 0° phase angle indicates that the material is purely elastic, i.e. solid like behaviour whereas a phase angle of 90° indicates that the material is purely viscous i.e. liquid like behaviour. The composition of matter of the present invention is typically a semi-solid or gel and therefore the phase angle is between 0 to 90° and may vary according to the required use of the material.

Preferably, the self-assembling peptide complexes form ribbons, fibrils, fibres or a three dimensional scaffold in a β-sheet tape-like substructure.

In some embodiments the composition of matter may be in the form of a gel, fluid, semi-solid, hydrogel, viscous solution, Newtonian fluid solution, aerogel, visco-elastic solid, xerogel, surface coating, film or a non-woven fabric (for example obtained by electrospinning in the presence of another polymer).

In all embodiments the self-assembling peptide complexes may comprise or be a SAP and a glycan that are not covalently bonded. The inventors have found surprisingly that covalent bonding between the SAP and GAG is not a requirement for the formation of a complex.

According to a second aspect of the invention there is provided a method of preparing a self-assembling peptide complex, the method comprising mixing at least one charged peptide capable of self-assembling having an overall net positive charge selected from the group comprising any one of SEQ ID NOs 1 to 10 or having a net negative charge selected from the group comprising any one of SEQ ID NOs 11 to 21, in a solution with a negatively charged polysaccharide in a selected ratio so as to form a gel.

It will be appreciated that the ratio of SAP to polysaccharide, for example GAG, can be varied according to the desired properties required of the resultant gel or gel like substance. Results presented hereinafter suggest that varying the ratios has a direct effect on rheological properties.

Preferably, the solution is saline based although any physiologically relevant solution used may be buffered or unbuffered.

Preferably, the SAP and polysaccharide are injected simultaneously into a recipient directly to the point at which it is desired to form a gel in situ. Alternatively, the peptides may be injected to the appropriate site before or after injection of GAG or a similar polysaccharide.

According to a third aspect of the invention there is provided an injectable biomaterial composition comprising a self-assembling peptide complex, the complex comprising:
(i) at least one charged peptide capable of self-assembling; and
(ii) an oppositely or same charged polysaccharide.

Preferably the charged peptide capable of self-assembling has either a net overall negative or positive charge and is selected from the groups identified hereinbefore.

Preferably, the injectable biomaterial composition forms a gel, semi-solid, hydrogel, viscous solution, visco-elastic solid, xerogel, surface coating or film at the site where it has been injected.

It will be appreciated that the biomaterial composition of the present invention may also be referred to as a pharmaceutical composition or a composition of matter.

According to a fourth aspect of the invention there is provided the self-assembling peptide complex of the first aspect of the invention or the biomaterial composition of the third aspect of the invention further comprising a bioactive peptide sequence attached on either or both of the peptide termini.

According to a fifth aspect of the invention there is provided the self-assembling peptide complex of the first aspect of the invention or the biomaterial composition of the third aspect for use as personal care products, as tissue reconstruction devices (e.g., dental reconstructive devices, disc, cartilage, meniscal tissue, tendon, ligaments and cardiovascular tissue), as a scaffold for tissue engineering or as an adjunct in ophthalmology procedures.

According to a sixth aspect of the invention there is provided the self-assembling peptide complex of the first aspect of the invention or the biomaterial composition of the third aspect for use in restoring biomechanical and biochemical functions of a variety of biological tissues.

According to a seventh aspect of the invention there is provided a method of repairing or replacing or restoring the nucleus pulposus of an intervertebral disc, the method comprising administering the self-assembling peptide complex of the first aspect of the invention or the biomaterial composition of the third aspect into an area of the nucleus pulposus of an intervertebral disc that requires treatment.

Preferably, the self-assembling peptide complex has similar mechanical properties to that of natural tissue, that is to say the shear elastic and viscous moduli are in the range of about 10 kPa for G' and about 4.5 kPa for G".

Accordingly to an eighth aspect of the invention there is provided a self assembling peptide complex or pharmaceutical composition comprising said complex, for use in treating back pain. Treating back pain may be achieved by repairing an intervertebral disc. Therefore, in embodiments the peptide complex may be for use in repairing an intervertebral disc. Treating or repairing the intervertebral disc may be achieved by replacing, rejuvenating or supplementing the nucleus pulposus of the intervertebral disc with the peptide complex of the present invention.

According to a ninth aspect of the invention there is provided a kit comprising a charged polysaccharide, at least one charged peptide of either the opposite or same charge as the polysaccharide and being capable of self-assembling and means for combining the polysaccharide and the peptide, wherein upon combination of the polysaccharide and the peptide a complex is formed, the kit optionally further including a set of written instructions.

Preferably the peptide complex has an elastic shear modulus (G') in the range 500 to 25,000 Pa.

Preferably, the polysaccharide is a GAG.

Preferably, the means for combining the GAG and the peptide may comprise or be a syringe comprising two barrels, wherein a first barrel comprises the GAG and a second barrel comprises the peptide and the first and the second barrels are adapted to be in fluid communication when the peptide and GAG are ejected from the syringe to allow mixing of the peptide and GAG.

All features ascribed to any one aspect of the invention apply mutatis mutandis to each and every other aspects of the invention.

BRIEF DESCRIPTION OF THE DRAWINGS

Embodiments of the invention are further described hereinafter with reference to the accompanying drawings, in which.

DETAILED DESCRIPTION

Figure 1:
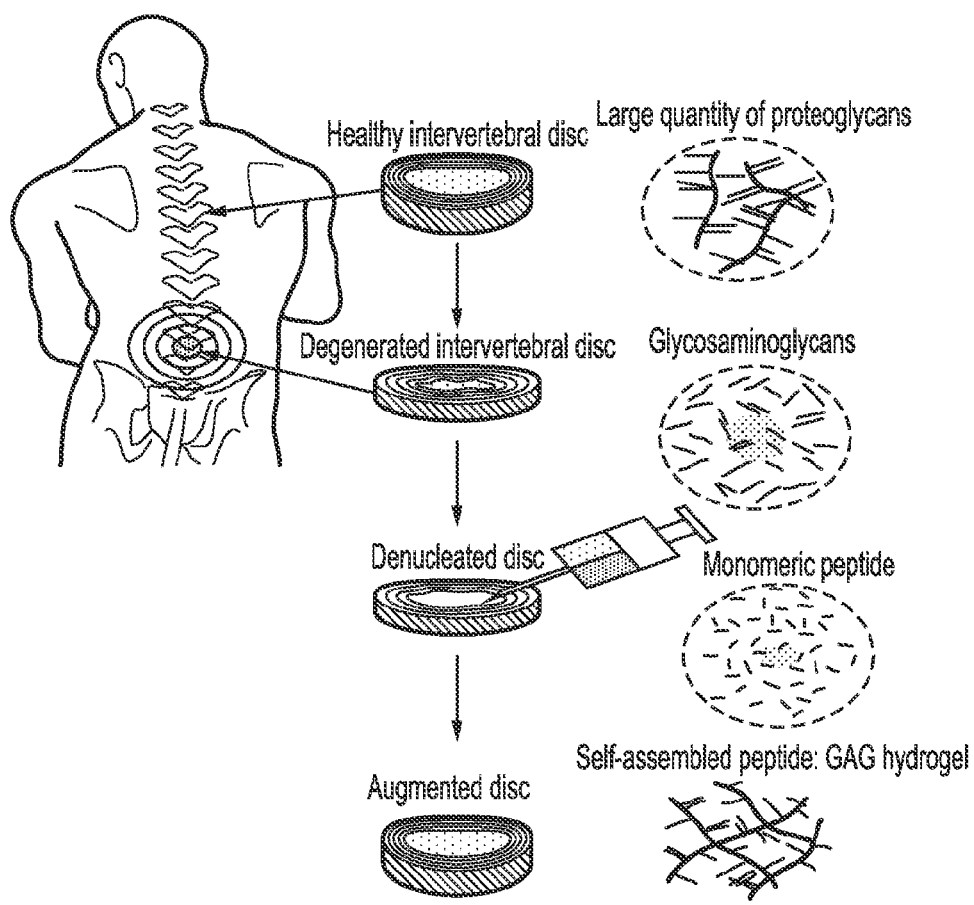
FIG. 1 shows a schematic representation of the degenerative changes in disc height, a denucleated disc and an augmented disc using the compositions of the present invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Reference herein to a "peptide" is to a short chain of amino acid monomers, in this application 11 amino acids, linked by peptide (amide) bonds, the covalent chemical bonds being formed when the carboxyl group of one amino acid reacts with the amino group of another.

Reference herein to a "peptide complex" refers to a composition of matter comprising two or more units wherein at least one unit is a peptide and the other unit is a GAG or mucopolysaccharide or polysaccharide.

Reference herein to "self-assembling" refers to the ability of the peptides and/or peptide complex to form ribbons, fibrils, fibres or a three dimensional network scaffold in a β-sheet tape-like substructure. Peptides of the present invention may self-assemble of their own accord or in the presence of an environmental or trigger or by the addition of a charged polysaccharide.

Reference herein to the "net charge per peptide" is in relationship to the total number of amino acid residues per peptide e.g. 2 net charges for an 11 amino acid residue peptide or 4 net charges for a 22 amino acid residue peptide. The term relates to the ratio of net charge to total amino acid residues rather than specific lengths of peptides.

Reference herein to "an overall net positive charge" refers to peptides with at least an approximate net +2 charge per peptide or more at a physiological pH.

Reference herein to "an overall net negative charge" refers to peptides with at least an approximate net −2 charge per peptide or more at a physiological pH.

Reference herein to "a physiological pH" is intended to refer to a pH range of between pH 4.0 to pH 8.0. In some regions of the body, for example in the region around a disc where there is a poor blood supply and a pooling of lactic acid the pH may be around 5.5 to 6.5.

Reference herein to an "oppositely or same charged polysaccharide" with respect to the peptide capable of self-assembling means that if the overall net charge of the peptide is positive the polysaccharide may be either positively or negatively charged. Alternatively, if the overall net charge of the peptide is negative the polysaccharide may be either negatively or positively charged.

In some embodiments of the invention the polysaccharide may not have a charge and may be an anionic polysaccharide.

Self-assembling peptides are believed to have a great potential in, for example and without limitation, the field of nucleus augmentation as they can be designed to be responsive with a wide range of chemical and mechanical properties.

As a starting point to developing a material suitable for the present invention, the self-assembly behaviour of several β-sheet tape forming peptides were evaluated, systematic investigations were carried out varying charge and hydrophobicity, in physiological-like conditions in order to establish design criteria for a peptide with a low c* and suitable mechanical properties.

An important factor in degeneration is the significant loss of swelling pressure from the disc, therefore a replacement biomaterial needs to have high water content and be able to retain this water. The natural tissue achieves this by the presence of a large number of negative charges on the proteoglycans chains, which causes an influx of small cations into the disc. This high salt content results in a high osmotic pressure within the disc. The negative charge density within the disc is due to the high concentration of proteoglycans and GAG chains, in particular chondroitin sulphate. It was hypothesised that it may be possible to mimic the comb like structures of the natural covalently bound proteoglycans through electrostatic interactions between charged polysaccharides and the various charged peptide analogues, therefore optimising the peptides further for this specific application.

It was important to assess the effect of GAG concentration on peptide self-assembly and gel properties.

In order to investigate the potential of the peptide:GAG hybrid hydrogels developed to satisfy the basic mechanical and leakage-resistant requirement for a nucleus augmentation material preliminary test were undertaken using a de novo ex vivo bovine caudal model. Bovine caudal discs were considered to be an adequate replacement, as those from C1 to C6 are representative of the size, biochemical makeup and elastic fibre organisation of healthy young human discs. Bovine discs have previously been used in numerous studies as a source of disc tissue and were deemed an appropriate model for initial investigations because they would allow comparison with the 'healthy' state, which ideally the treatment would attempt to replicate.

Peptides

All peptides were stored at −20° C. as freeze-dried white fluffy powders. Table 1 below lists the peptides

| PEPTIDE NAME | SEQUENCE | CHARGE |
| --- | --- | --- |
| $P_{11}$-4 (SEQ ID NO: 11) | $CH_3CO$-Q-Q-R-F-E-W-E-F-E-Q-Q-$NH_2$ | −2 |
| $P_{11}$-8 (SEQ ID NO: 1) | $CH_3CO$-Q-Q-R-F-O-W-O-F-E-Q-Q-$NH_2$ | +2 |
| $P_{11}$-9 (SEQ ID NO: 12) | $CH_3CO$-S-S-R-F-E-W-E-F-E-S-S-$NH_2$ | −2 |
| $P_{11}$-12 (SEQ ID NO: 2) | $CH_3CO$-S-S-R-F-O-W-O-F-E-S-S-$NH_2$ | +2 |
| $P_{11}$-13 (SEQ ID NO: 13) | $CH_3CO$-E-Q-E-F-E-W-E-F-E-Q-E-$NH_2$ | −6 |
| $P_{11}$-14 (SEQ ID NO: 3) | $CH_3CO$-Q-Q-O-F-O-W-O-F-O-Q-Q-$NH_2$ | +4 |
| $P_{11}$-15 (SEQ ID NO: 14) | $CH_3CO$-N-N-R-F-E-W-E-F-E-N-N-$NH_2$ | −2 |
| $P_{11}$-16 (SEQ ID NO: 4) | $CH_3CO$-N-N-R-F-O-W-O-F-E-N-N-$NH_2$ | +2 |
| $P_{11}$-17 (SEQ ID NO: 15) | $CH_3CO$-T-T-R-F-E-W-E-F-E-T-T-$NH_2$ | −2 |
| $P_{11}$-18 (SEQ ID NO: 5) | $CH_3CO$-T-T-R-F-O-W-O-F-E-T-T-$NH_2$ | +2 |
| $P_{11}$-19 (SEQ ID NO: 6) | $CH_3CO$-Q-Q-R-Q-O-Q-O-Q-E-Q-Q-$NH_2$ | +2 |
| $P_{11}$-20 (SEQ ID NO: 16) | $CH_3CO$-Q-Q-R-Q-E-Q-E-Q-E-Q-Q-$NH_2$ | −2 |
| $P_{11}$-24 (SEQ ID NO: 17) | $CH_3CO$-S-S-R-Q-E-Q-E-Q-E-S-S-$NH_2$ | −2 |

-continued

| PEPTIDE NAME | SEQUENCE | CHARGE |
|---|---|---|
| $P_{11}$-25 (SEQ ID NO: 18) | $CH_3CO$-S-S-R-S-E-S-E-S-E-S-S-$NH_2$ | -2 |
| $P_{11}$-26 (SEQ ID NO: 7) | $CH_3CO$-Q-Q-O-Q-O-Q-O-Q-O-Q-$NH_2$ | +4 |
| $P_{11}$-27 (SEQ ID NO: 19) | $CH_3CO$-E-Q-E-Q-E-Q-E-Q-E-Q-E-$NH_2$ | -6 |
| $P_{11}$-28 (SEQ ID NO: 8) | $CH_3CO$-O-Q-O-F-O-W-O-F-O-Q-O-$NH_2$ | +6 |
| $P_{11}$-29 (SEQ ID NO: 20) | $CH_3CO$-Q-Q-E-F-E-W-E-F-E-Q-Q-$NH_2$ | -4 |
| $P_{11}$-30 (SEQ ID NO: 21) | $CH_3CO$-E-S-E-F-E-W-E-F-E-S-E-$NH_2$ | -6 |
| $P_{11}$-31 (SEQ ID NO: 9) | $CH_3CO$-S-S-O-F-O-W-O-F-O-S-S-$NH_2$ | +4 |
| $P_{11}$-32 (SEQ ID NO: 10) | $CH_3CO$-O-S-O-F-O-W-O-F-O-S-O-$NH_2$ | +6 |

Preparation of Peptide Solutions

Solutions of peptides were prepared directly in either $D_2O$ or $H_2O$ containing either 130 or 200 mM NaCl or PBS. Peptide concentrations in the millimolar range given for the NMR studies were values multiplied by an appropriate factor to account for the actual percentage peptide content. The samples were vortexed for 20 seconds, and then sonicated for 15 minutes. Solution pD was measured and adjusted to either 7.4 or 6.0±0.5 using a calibrated pH meter and the relation pD =pH meter reading +0.417. Any adjustment of pD, if necessary, was made with minimal μL volumes of either HCl or DCl and/or either NaOH or NaOD. Finally, solution vials were closed, sealed with PTFE tape, and then warmed to approximately 80° C. to maximise peptide solubility. Solutions were left to equilibrate at room temperature.

High Resolution $^1$H-NMR Study of Peptide Self-Assembly as a Function of Concentration (2,2,3,3-d4)-trimethylsilyl-3-propionic acid (TMSP, chemical shift 0 ppm) an internal reference standard was added to all peptide solutions. NMR data were acquired at room temperature. A pre-saturation program was used to minimize the water peak, and 1024 scans were measured per spectrum. Sample spectra were recorded at various timepoints after preparation to ensure the solutions had reached stable equilibrium. The aromatic multiplet at chemical shift 6.9-7.8 ppm was integrated, relative to the reference peak.

Preparation of Peptide:Glycosaminoglycan Gels.

The concentration of peptide was kept constant for each sample (20 mg/ml) and the molar ratio of GAG subunit to one peptide was increased. The samples were named by the number of GAG subunits to each peptide present e.g. P11-12:GAG 1:10=one P11-12 peptide monomer to ten GAG dimer subunits. GAG was added to peptide solutions after preparation as stated above. The mixtures were vortexed as heated again to ensure complete mixing.

Rheological Study of Peptide:Glycosaminoglycan Gels

Measurements were performed using a cone-plate geometry (cone angle: 1°, diameter: 50 mm, gap: 0.033 mm). All the tests were performed at 25° C., utilizing a solvent trap and the atmosphere within was kept saturated to minimize evaporation of the peptide samples. To ensure the measurements were made in the linear viscoelastic regime (LVER), amplitude sweeps were performed in a shear strain controlled mode from 0.01-100%. Two amplitude sweeps were carried out for each sample (1 Hz and 20 Hz) and a strain level was chosen at which the elastic modulus (G') and viscous modulus (G") were independent of strain amplitude at the two different frequency levels. The dynamic moduli of the hydrogels were measured as a frequency function with the sweeps carried out between 1 and 20 Hz. Samples were allowed to equilibrate for 15 minutes once loaded prior to the start of testing. Fresh samples were used for the amplitude and frequency sweeps. After the frequency sweeps, two more amplitude weeps (1 Hz and 20 Hz) were carried out in a stress controlled mode to confirm the testing was performed within the LVER. The stress range was chosen based on the stress values from the frequency sweeps at 1 and 20 Hz: if these two values were then independent of stress amplitude, then this confirmed that testing was within the LVER.

Transmission Electron Microscopy Study of Peptide: Glycosaminoglycan Gels

Electron microscope (EM) grids (copper 300 mesh) were coated with carbon prior to use, by the flotation of a carbon film from a mica sheet onto the grids. The EM grids were then glow discharged prior to sample application to ensure adhesion of the sample to the EM grid. Peptide gels prepared in phosphate buffered saline solution were quickly diluted by various factors in pure water. The EM grids were touched onto the peptide solutions for one minute. The grid was air-dried and then negatively stained with uranyl acetate solution (4% w/v) for 20 seconds and air-dried. TEM images were obtained using a Philips CM10 electron microscope operating at 80 kV accelerating voltage. Images were obtained quickly to avoid artefacts and destruction of the sample.

Ex Vivo Model Specimen Preparation

Bovine tails were harvested from calves aged less than 30 months (typically 24-28 months) and to avoid potential damage to the tissue, the discs were maintained at 2-8° C. prior to experimentation. The caudal intervertebral discs (C1-C6) discs with only the distal endplate still attached were isolated from the tail. Discs were placed in monosodium citrate solution to remove excess blood and through swelling pressures help differentiate the nucleus pulposus from the annulus fibrosus tissue. The discs were then removed from the solution and the nucleus pulposus tissue was excised. The disc and nucleus tissue were weighed prior to and post removal. Discs were then attached to lightly sanded artificial Perspex endplates (2×40×40 mm).

Preparation of Samples and Method of Augmentation

GAG only

1:2 and 1:10 Equivalent Injected

PBS was added to the weighed out chondroitin-6-sulphate. The solution was vortexed for 1 min until all the powder was dissolved. 250 μl of solution was then injected into a disc using a 25 G needle and syringe with a second 25 G needle as an air hole.

1:100 Equivalent Added as Gel

PBS was added to a weighed amount chondroitin-6-sulphate. The solution was vortexed for 1 min and resulted in a very viscous, gel-like liquid. The gel was then added to the disc prior to endplate attachment using a spatula and the disc weighed before and after to determine the amount added. The artificial endplate was then attached and the disc punctured with a 25 G needle to mimic the injection.

P11-12:GAG

1:2 and 1:10 Injected

A 40 mg/ml solution of P11-12 was prepared in PBS, vortexed for 1 min and heated until the solution was a clear liquid. It was then injected into each disc using a 25 G needle and syringe with a 25 G needle as an air hole followed by a 125 μl injection of GAG solution (prepared in PBS and vortexed for 1 min). The CS injection was through the 25 G needle that had previously been used as the air hole and with the needle used for the P11-12 injection as the new air hole.

1:100-P11-12:GAG

A 1:100 gel was prepared then placed in the disc prior to endplate attachment. Discs were punctured with 25 G needle to mimic injection. A 20 mg/ml solution was prepared in PBS, vortexed for 1 min and sonicated for 15 mins then pH adjusted to 7.4. The gel was then heated at 80° C. until the solution became a clear liquid and then chondroitin-6-sulphate was added and vortexed. The gel was then added to the disc prior to artificial endplate attachment using a spatula and the disc weighed before and after to determine the amount added. The artificial endplate was then attached and the disc punctured with a 25 G needle to mimic injection.

Quantification of Glycosaminoglycan Accumulation in PBS

In order to quantify the amount of GAG leaked from the discs over a 48 hour time period, after the GAG or P11-12:GAG additions to the discs were carried out. Test samples comprised GAG only 1:10 and 1:100 gel P11-12:GAG 1:10 and 1:100 gel. Discs were placed in 30 ml of PBS on an orbital shaker for 48 hours. 3 ml of PBS was removed at 24 and 48 hours. Disc denuclueated then repacked with removed nucleus pulposus tissue N=3 time points. The 3 ml PBS samples from each disc at the two timepoints were analysed via a standard DMMB assay using chondroitin sulphate to construct the standard curve.

Peptide Dissolution 2.5 ml of 130 mM NaCl, D$_2$O, pD 7.4 supernatant was added on top of the SAP:GAG gels. The concentration of peptide dissolved into the supernatant as a function of time was determined via UV spectroscopy. The UV wavelength of 279 nm corresponds to the electronic citation of the idol side chain of the tryptophan residue, found in position 6 of the SAP, and so this can be used to determine the molar concentration of the peptide taking into account the molar extinction coefficient of the tryptophan residue.

Static Loading Study.

For this study the disc were prepared as above but with approx 10 mm of vertebra still attached to the distal endplate. Following preparation, all discs were sealed in individual plastic bags with PBS soaked tissue paper to prevent samples drying and stored at 2-8° C. overnight. The distal vertebra section of each sample was then cast in 70 mm diameter polymethylmethacrylate (PMMA) cement to produce a flat surface that was parallel to the Perspex endplate. Once set, the samples were stored in individual sealed plastic bags containing PBS soaked tissue paper at 2-8° C. until testing. All specimens underwent static axial compressive loading from 0 to 9 kN using displacement control at a low load rate of 1 mm/min. It should be noted that at the start of each test, the fixture on the crosshead of the materials testing machine was brought into contact with the Perspex endplate until a load of 0.3 N was recorded. At this point, the displacement and load was then re-zeroed and the test was started.

Calculation of the Normalised Stiffness.

In this study, the gradient of the linear part of the load vs. displacement plot was taken between 200-500 N to give the stiffness F/δ=k. Then the normalised stiffness or apparent modulus for each disc in this load region was determined using the following formula:

$$\text{Normalised stiffness} = \frac{kl}{A}$$

Where k=stiffness, A=area and l=length.

The areas and lengths were determined by taking measurements from photographs taken of each of each discs prior to testing. The normalised stiffness value was calculated for each disc and then the average of the 6 discs for each sample type was taken.

EXAMPLE 1

Experiments were conducted to optimise peptides capable of self-assembly further by mixing them with GAGs to form self-assembling peptide complexes. It is believed that it is the loss of GAGs during intervertebral disc degeneration which leads to reduction in hydration and then subsequently a loss in swelling pressure and disc height both of which can result in altered spinal mechanics and in some cases patient pain. It was hypothesised that by mixing the charged GAG chains with the charged peptides they would interact through electrostatic interactions to form a comb like structure similar to that of the natural proteoglycans found within the disc (see FIG. 1 which shows a schematic representation of the degenerative changes in disc height, a denucleated disc and an augmented disc using the compositions of the present invention.). Results showed that the peptides still undergo self-assembly often forming cloudy/opaque gels which suggests the presence of larger particulates forming. The GAGs also act as an additive actually triggering the onset of gelation in many instances. Gels exhibited excellent stability.

Figures 2A, 2B:
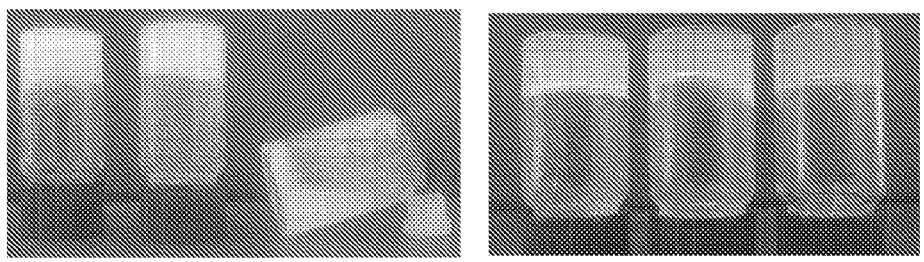
FIG. 2A shows gelation left to right P11-8:CS 1:10, 1:2 and P11-8.
FIG. 2B shows gelation left to right P11-12:CS 1:10, 1:2 and P11-12.
Figures 2C, 2D:
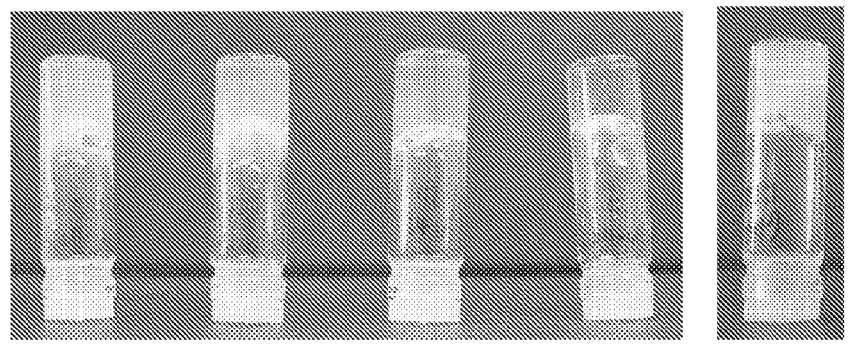
FIG. 2C shows gelation of left to right P11-14:CS 1:20, 1:10, 1:2 and 1:1.
FIG. 2D shows gelation of P11-28:CS 1:100.

P11-8 takes days to form a self-supporting gel but in the presence of GAG this can be reduced down to minutes (FIG. 2A). P11-12 takes minutes to form a self-supporting gel at 20 mg/ml but in the presence of GAG this can be reduced to spontaneous on mixing (FIG. 2B). As the GAG concentration is increased the gels become more opaque suggesting large molecules/particles/aggregates have been formed. At 20 mg/ml P11-14 does not self-assemble but the addition of 1:1 GAG resulted in self-assembly and gelation (FIG. 2C). Again at 20 mg/ml P11-28 does not self-assemble but the addition of 1:100 GAG resulted in self-assembly and gelation (FIG. 2D).

Figure 3A:
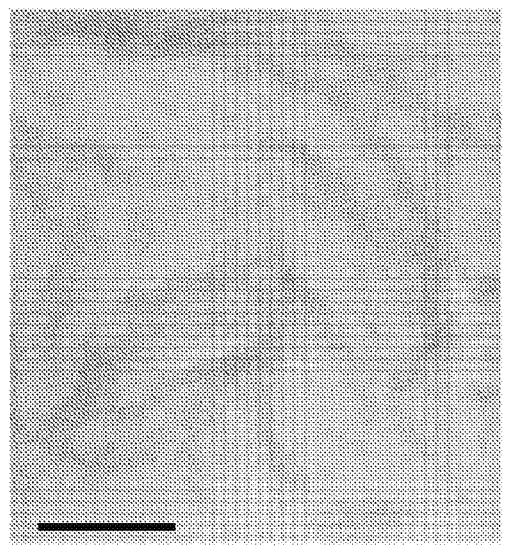
FIG. 3A shows electron microscopy of background network of ribbons of a self-assembly peptide.
Figure 3B:
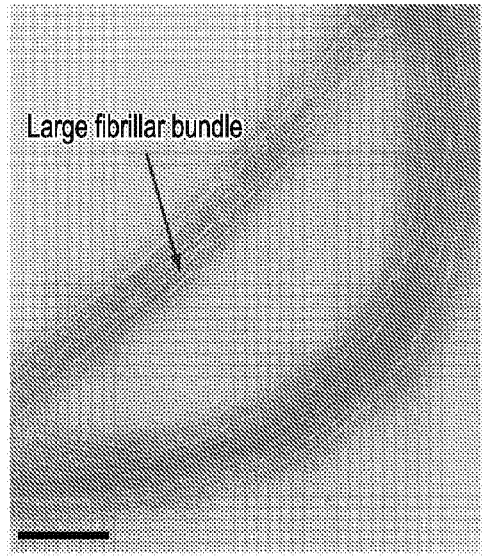
FIG. 3B shows the effect on fibrilar bundle formation by the addition of GAG (scale bars=200 nm).

It was found that the addition of GAG chains to the peptides did not disrupt their self-assembly and in some cases actually acts as a trigger to self-assembly. GAG chains also affect the aggregate morphologies, often leading to larger fibrillar bundle structures (see FIG. 3A compared to FIG. 3B), which is the reason for the more opaque gels. Surprisingly, GAGs act as an additive improving the rheological properties of the gels and also affect the gelation kinetics. Results demonstrate that the addition of GAG provides a wide range of mechanical properties and that GAG can, in some instances make the brittle peptide gels elastic by acting as a flexible cross-linker.

Figure 4A:
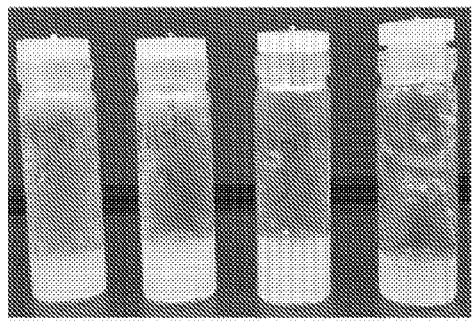
FIG. 4A shows vials containing P11-12 prior to mixing (left hand side) and four vials with different polysaccharides from left-right-Chondoritin-4-Sulphate (C4S), Chondroitin-6-Sulphate (C6S), Low molecular weight dextran (LMwD) and High molecular weight dextran (HMwD).
Figure 4B:
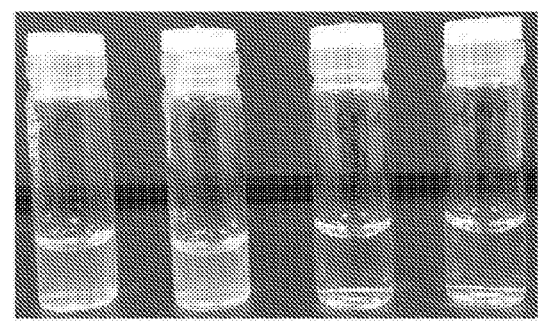
FIG. 4B shows post mixing of P11-12 and different polysaccharides, vials inverted to demonstrate self-supporting gel.
Figure 4B:
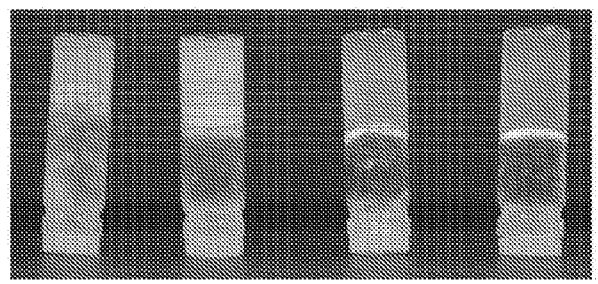

The gelling properties of other negatively charged polysaccharides with SAPs were investigated. FIG. 4A shows four vials containing P11-12 prior to mixing (left hand side) and four vials with different polysaccharides from left-right-Chondoritin-4-Sulphate (C4S), Chondroitin-6-Sulphate (C6S), Low molecular weight dextran (LMwD) and High molecular weight dextran (HMwD) (right hand side). FIG. 4B shows post mixing vials inverted. Samples were 1.5 ml, 1:10 P11-12:polymer, in PBS with 0.04% NaN$_3$ pH 7.4. Results show that the addition of negatively charged polysaccharides to P11-12 does not inhibit self-assembly and, as was the case with C6S, the other polysaccharides tested seem to speed up gelation suggesting they may also be lowering the peptide c*.

EXAMPLE 2

Tests were conducted to provide a peptide gel of similar stiffness to that of the nucleus pulposus. Rheometry was carried out on the peptide gels in PBS at 20 mg/ml. Amplitude sweeps were first carried out to determine the LVER region. For P11-8 and P11-12 peptide only it was observed when trying to unload the sample from the rheometer that the top cone could not be easily raised suggesting the gel had an extremely strong molecular structure that was difficult to break and hence pull apart. The plateau elastic modulus G' and phase angle θ are given in Table 2 below.

| Peptide | G'$_N$° (kg m$^{-1}$s$^{-2}$) | Phase angle | J (nm) |
|---|---|---|---|
| P$_{11}$-8 | 5,221 | ~8° | 11.6 |
| P11-8:GAG 1:10 | ~200 | ~9° | 33 |
| P$_{11}$-12 | 22,285 | ~9° | 7.2 |
| P11-12:GAG 1:10 | ~11,000 | ~8° | 8.7 |

Figure 9:
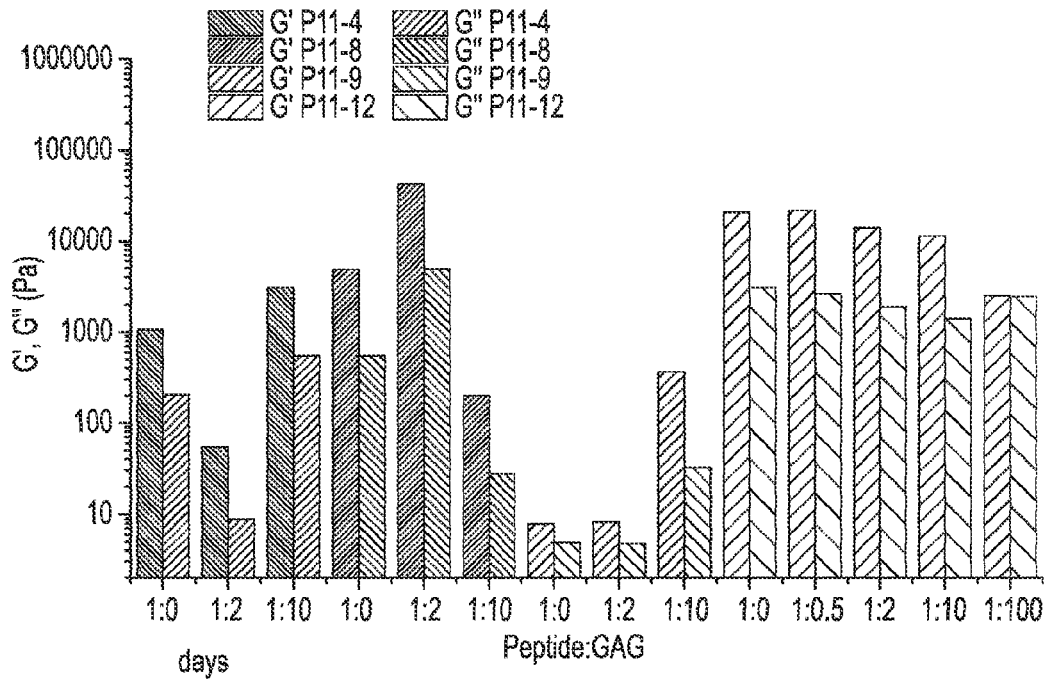
FIG. 9 shows elastic and viscous modulus at 2 Hz (walking frequency) for peptide:GAG complexes

Table 2 shows a comparison of the plateau elastic modulus and lower limit of the distance between nearest cross links (j) in the peptide gels. (g$_N$=1±0.2, f>4, k$_B$=1.38×10$^{-23}$ m$^2$ kg s$^{-2}$ K$^{-1}$, T=298K) for P11-8 and P11-12 on their own and when mixed with GAG. Data indicates that P11-12 forms the stiffest gel. Using a model taken from the rubber-like elasticity theory, the magnitude of the plastic elastic modulus can be used to extract information about the mesh size of the peptide network and therefore the crosslink density. The lower limit of the distance between nearest cross links (j) has been calculated for each peptide. FIG. 9 demonstrates the effect of GAG ratio on the G' and G" of the peptide:GAG complexes From the calculated j values it is clear to see how the mesh size affects the mechanical properties of the gels. The stiffer gels have shorter distances between crosslinks and therefore a greater number of crosslinks in the network per unit volume.

EXAMPLE 3

The effects of mixing chondroitin sulphate GAG with the peptides were investigated. It was hypothesised that the charged GAG chains would interact electrostatically with the charged peptides. To establish whether such an interaction was possible, visual observations of a systematic mixing study was carried out and the morphology of the aggregates formed during mixing studied using TEM.

P11-4:
Peptide:GAG ratios from 1:2 to 1:10 were investigated. At all GAG ratios, self-supporting gels were formed. However, as the GAG concentration was increased, the quality of the gel differed and the gels became cloudier in appearance. The addition of GAG reduced the samples' gelation time from hours to seconds P11-8:
Peptide:GAG ratios from 1:2 to 1:10 were investigated. The addition of GAG to P11-8 led to faster gelation, with self-supporting gels forming on the day of preparation compared to the control sample which took days.

P11-9:
Peptide:GAG ratios from 10:1 to 1:10 were investigated. Self-supporting gels were formed at all GAG molar ratios). However, as the GAG concentration was increased the quality of the gel differed and the gels became more turbid and inhomogeneous. The 1:10 sample was a very turbid milky gel. At a GAG ratio of 1:2 subunits and higher, a lot of heating and vortexing was required to enable the GAG to dissolve. However, once the GAG was dissolved and the heating stopped, the gelation time of the samples was decreased from minutes to seconds even while the samples were still warm. After a year, the P11-9 control was still a self-supporting gel alongside the lowest GAG concentration.

However, as the GAG concentration increased the gel quality was once again reduced. From a ratio of 1:0.2 and upwards phase separation occurred and a gel-like precipitate was observed alongside a clear liquid phase. At the higher ratios in some cases, such as 1:10 and 1:3, a large self-supporting gel phase was still visible.

After approximately four and a half months, three representative samples were chosen to be studied by TEM. Peptide:GAG ratios of 1:0.5, 1:2 and 1:10 were compared to the GAG and peptide control samples. In the GAG control sample, the main structures seen were amorphous with no well defined structures. In the P11-9 control sample a background carpet of ribbon structures was seen with ribbons having a width of 3-5 nm. At a low GAG ratio of 1:0.5, a ribbon network was observed in the background of the image with larger, undefined fibrillar structures visible. The widths of large bundles varied from around 60 to 75 nm, and the widths of the individual ribbons were around 5 nm. An image was also taken of the undiluted sample, although the finite structures could not be clearly identified, it was possible to identify the porous and intertwined structure of the gel. At a medium GAG ratio of 1:2, again the ribbon network was observed in the background of the image with larger, undefined fibrillar structures visible. The width of these larger bundles varied from 30 to 100 nm and the background ribbons varied in width between 2 and 6 nm. In the high GAG ratio sample of 1:10, the background ribbon network was observed again with larger, undefined fibrilar structures visible. However, the larger bundles of ribbons were less commonly seen than with the lower GAG ratios. The width of these large bundles was around 100 to 130 nm and the width of the background ribbons was approximately 4 nm.

In summary, in the 1:0.5 sample there was a very high density of bundles of ribbons forming undefined fibril like structures. In the 1:2 sample, there was mainly a background network of ribbons with very long bundles ½ width of a TEM grid in length and again in the 1:10 sample there was mainly a background network of ribbons visible with fewer but larger bundles present. As is the case with no GAG present, this peptide in the presence of GAG forms mainly ribbon structures with no well defined fibrils. However it was observed that the loose bundling of ribbons was reduced in the presence of GAG.

P11-12:

Peptide:GAG ratios from 0.1 to 1:100 were investigated. At all GAG ratios self-supporting gels were formed, although as the GAG concentration was increased the quality of the gel differed and the gels became less turbid and "bitty" over the mid range ratios. Once above 1:20 the gels became more turbid and bitty again with the 1:100 ratio being a very thick gel. The addition of a small ratio of GAG increased the gelation time from minutes to hours, but the addition of a GAG ratio of 1:1 and above took the gelation time down to seconds, with gelation in a ratio of 1:20 and above happening spontaneously upon mixing. At nearly two years, all gels were still self-supporting showing remarkable stability. The midrange ratios had less bitty gels on the walls of the vials. The 1:100 was by far the thickest gel and showed a yellow colour due to the GAG. After approximately five and a half months, three representative samples were chosen to be studied by TEM. Peptide:GAG ratios of 1:0.5, 1:2 and 1:5 were compared to the GAG and peptide control samples. In the P11-12 control sample diluted down to approximately 5000 µM (7 mg/ml), the main structures seen were nanotubes with an external diameter of 20 to 39 nm. In the P11-12 control sample diluted down to approximately 20 µM, the main structures observed were again tubular structures with a width of 25±2 nm and a twist pitch of ~165 nm, there was also a presence of helical structures with a twist pitch of approx 230 nm and a width of 15 to 40 nm. In the 1:0.5 ratio sample, fibril structures were observed with a width of 15 to 30 nm and a background network of ribbons of width 2 to 3 nm. There was also the presence of an amorphous aggregate structure. In the 1:2 sample, there was a background network of ribbons with an average width of around 4 nm with larger fibrillar bundles varying in width from 8 to 40 nm. There was also a presence of needle like structures with a very uniform width of 60 to 90 nm. In the 1:10 sample, the edge of a large fibril network can be seen. Once again, the presence of needle like structures could be seen that varied in width between 60 and 150 nm.

EXAMPLE 4

Experiments were conducted to study peptide analogues, systematically varying in charge and hydrophobicity to establish the design criteria for a low critical concentration for aggregation know as the $c^*$. This should not only result in a low background monomer concentration but also lead to more cost effective medical devices.

High resolution solution $^1H$ NMR was used to follow the self-assembly of the peptides in physiological-like solutions as a function of time. To measure self-assembly, the line width broadening of the NMR spectra is exploited. The population of peptide in an aggregated state gives rise to spectra that are so broad that they are lost in the baseline; in contrast, the population of peptide in monomeric state gives rise to high resolution spectra. By integrating the splitting pattern arising from the aromatic region and normalising it with respect to the peak observed due to a known standard, the fraction of monomer can be estimated.

Figures 5A, 5B:
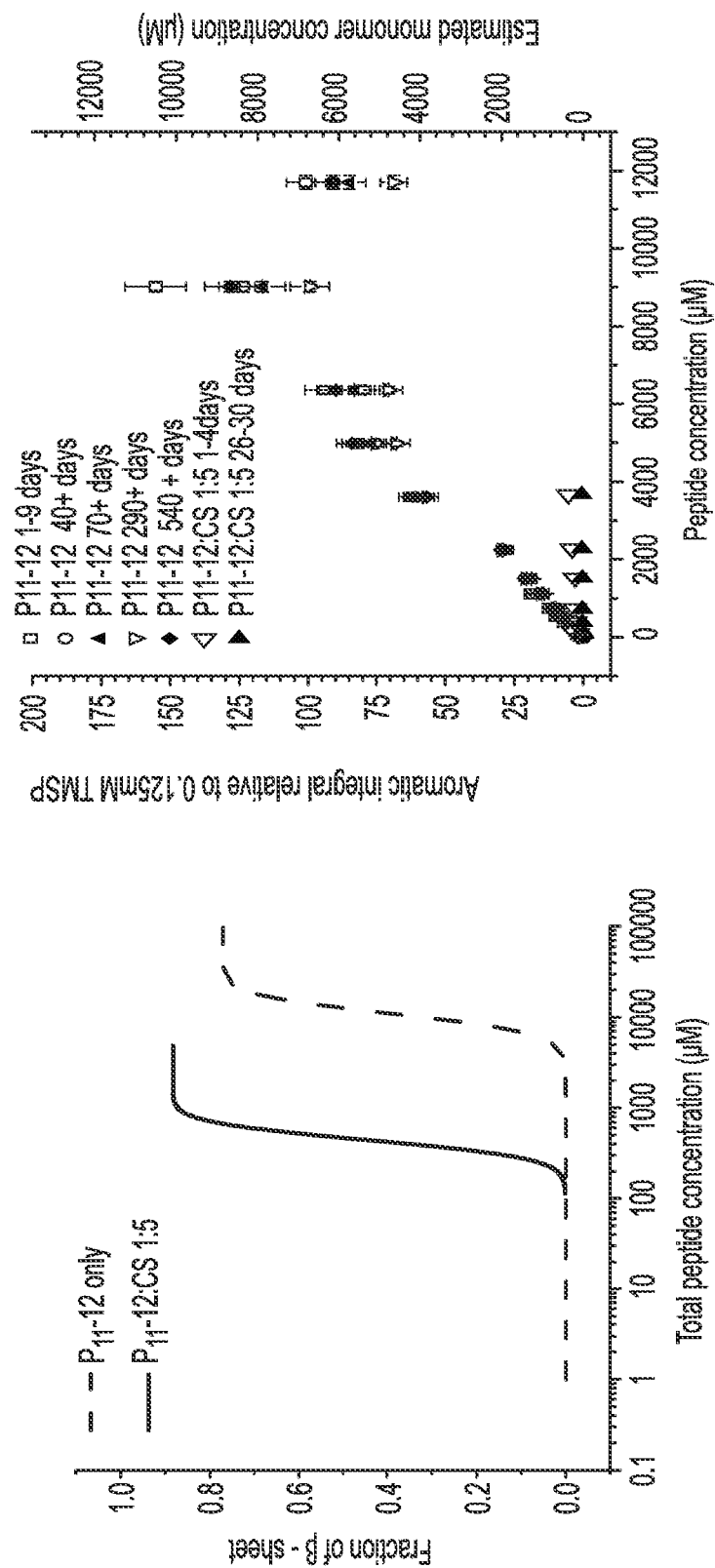
FIG. 5A shows the estimated equilibrium self-assembly curve for P11-12 and P11-12:CS 1:5.
FIG. 5B shows the $^1$H NMR aromatic region integral of P11-12 relative to integral of 0.125 mM TMSP reference peak as a function of increasing total peptide concentration and time from sample preparation

Estimated equilibrium self-assembly curves for P11-12 and P11-12:CS 1:5, i.e. fraction of peptide in self-assembled state as a function of increasing total peptide concentration with and without GAG present in a ratio of 1:5 is shown in FIG. 5A, demonstrating the effect of the presence of GAG to the peptide self-assembly profile and a dramatic decrease in $c^*$. FIG. 5B shows the $^1H$ NMR aromatic region integral of P11-12 relative to integral of 0.125 mM TMSP reference peak as a function of increasing total peptide concentration and time from sample preparation. This data demonstrates that in the presence of GAG the equilibrium state is reached much faster, without GAG it takes around 1 month but with GAG this happens in less than 4 days. The fact that there is a difference with and without GAG suggests there is an interaction occurring.

Figure 6:
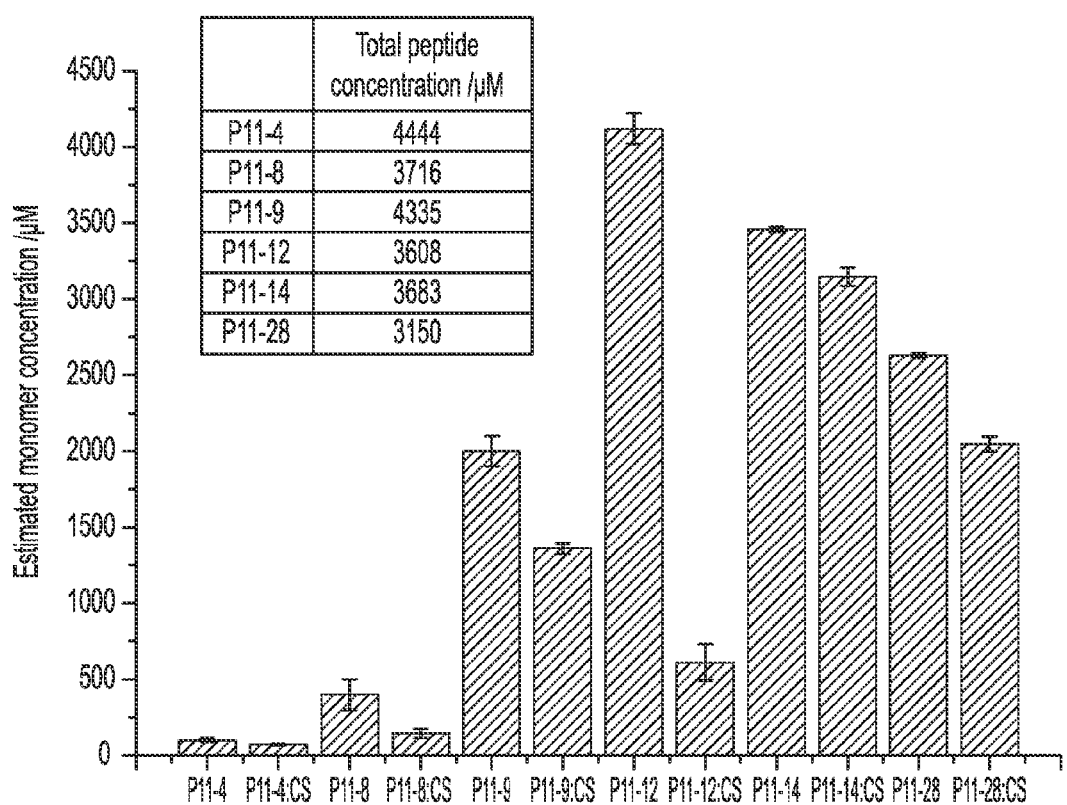
FIG. 6 shows a plot of estimated monomeric peptide concentration in a sample ~5000 µM for peptide only and peptide:GAG 1:10. Actual peptide concentrations inside samples taking into account peptide content in table insert on plot.

The $c^*$ values were determined by peptide primary structure and P11-4, P11-8, P11-9 and P11-12 underwent a random coil to β-sheet conformational change. Based on the theory of surfactant self-assembly the amount of monomer present at any concentration below $c^*$ will be 100% and above $c^*$ will be the equivalent concentration to $c^*$. This indicates that a peptide with a high $c^*$ will have a higher amount of monomer always present than for a peptide with a low $c^*$. FIG. 6 shows a plot of estimated monomeric peptide concentration in a sample ~5000 µM for peptide only and peptide:GAG 1:10. This data demonstrates the effect of GAG on peptide $c^*$ as at this high a total peptide concentration according to surfactant theory the background level of monomer should be equal to the $c^*$. This data again supports evidence of an interaction between the peptide and GAG.

Figure 7:
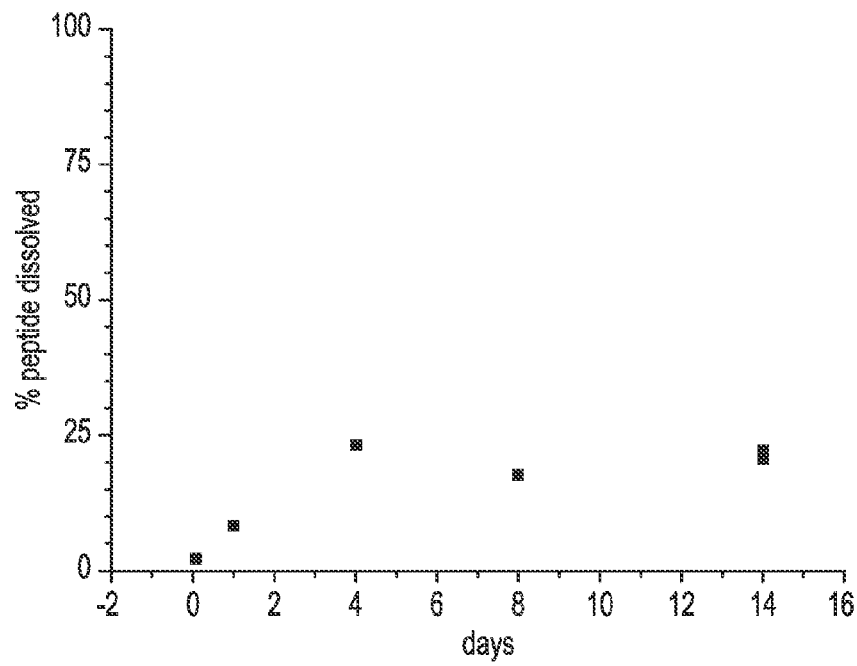
FIG. 7 shows percentage of P11-12:C6S gel that dissolved into supernatant over a 14 day period.

In order to further exemplify the effect of GAG on SAP self-assembly a dissolution study was carried out. The higher the peptide $c^*$ the greater the level of monomer there is to dissolve from the gel. FIG. 7 demonstrates the percentage of peptide leaked from a P11-12 20 mg/ml peptide:GAG (1:10) gel over a 14 day period. Overall peptide dissolution from the gel was 20% and the dramatic effect of the GAGs presence can be seen at 3-4 days when with a peptide only gel 39.9±9.15% dissolves whereas in the presence of the GAG only 20±10% dissolves away.

EXAMPLE 5

The rheological properties of the peptide:GAG samples were examined and compared to the rheological properties of peptides alone to establish how the addition of GAG affected the material properties of the gels. The frequency sweeps from the study (data not shown) for the various peptide:GAG combinations can be summarized as follows: $P_{11}$-4: GAG and viscous modulus vs. frequency, starting frequency 1 Hz, end frequency: 20 Hz, strain controlled: 0.15% (control), 0.175% (1:2) and 0.04% (1:10). Temp: 25° C. 20 days old. $P_{11}$-8:GAG elastic and viscous modulus vs. frequency, starting frequency 1 Hz, end frequency: 20 Hz, Strain controlled: 0.1% (1:2 and 1:10), Temp: 25° C., 1.5 months old. $P_{11}$-9:GAG elastic and viscous modulus vs. frequency, starting frequency 1 Hz, end frequency: 20 Hz, Strain controlled: 0.5%, Temp: 25° C. $P_{11}$-12:GAG Elastic and viscous modulus vs. frequency, starting frequency 1 Hz, end frequency: 20 Hz, Strain controlled: 0.25% (1:0.5), 0.1% (1:2), 0.05% (1:10), 0.15% (1:100), Temp: 25° C. 1:0.5, 1:2 and 1:10 2 months old and 1:100 6 days old.

P11-4:

First of all, amplitude sweeps were carried out at two frequencies to determine the LVER. By comparing the amplitude sweeps for both samples it could be seen that the 1:2 gel had a slightly greater LVER indicating the gel could undergo higher strains before there was a breakdown in molecular structure, i.e. a more mobile or looser gel. From the amplitude sweeps, a strain value of 0.175% was chosen within the LVER to carry out the frequency sweep for the 1:2 sample and 0.04% for the 1:10 sample. The frequency sweeps for these two samples are compared to the P11-4 control. As with P11-4 on its own, for both GAG ratios, the elastic modulus was higher than the viscous modulus, suggesting the sample had more solid than liquid-like behaviour. The shape of the plot is typical of that of a gel although the increase of the phase angle from 7-14° for 1:2 and 9-13° for 1:10 suggests viscoelastic solid behaviour. The addition of a small amount of GAG (1:2) decreased the stiffness of the hydrogel formed. However, as the GAG concentration was increased further (1:10), the hybrid gels became stiffer than gels of the peptide alone.

P11-8:

It was observed that upon loading, the 1:2 gel seemed to split into a liquid and gel phase as with the control. It was also noted that when trying to unload the sample from the machine, the top cone of the rheometer did not easily separate from the sample, suggesting a strong molecular structure that was difficult pull apart. Also when the gel was wiped off the rheometer with tissue, the gel formed a substance on the tissue, which looked and felt like candle wax. Amplitude sweeps were carried out at two frequencies to determine the LVER. By comparing the amplitude sweeps for both samples, it was observed that the 1:10 sample had a slightly greater LVER indicating a mobile gel. From the amplitude sweeps, a strain value of 0.1% was chosen within the LVER for both the samples to carry out the frequency sweeps. The resulting frequency sweeps for these two samples were compared to the P11-8, both the frequency sweeps showed the gels had solid-like behaviour with higher elastic than viscous modulus. The addition of a small amount of GAG (1:2) caused both moduli to greatly increase by over an order of magnitude. The elastic modulus for this peptide/GAG combination was the highest determined of those tested at nearly 50 kPa. The shape of this plot was typical for that of a gel and it had more solid-like than liquid-like behaviour with an average phase angle of ~7°. However, as the GAG concentration was increased further (1:10), the gels actually became weaker than the peptide gel on its own. The increased viscosity was not only shown in the decreased moduli of the 1:10 sample, but also in the increase of its phase angle)(~9°) as well, again showing less solid-like behaviour.

Figure 8:
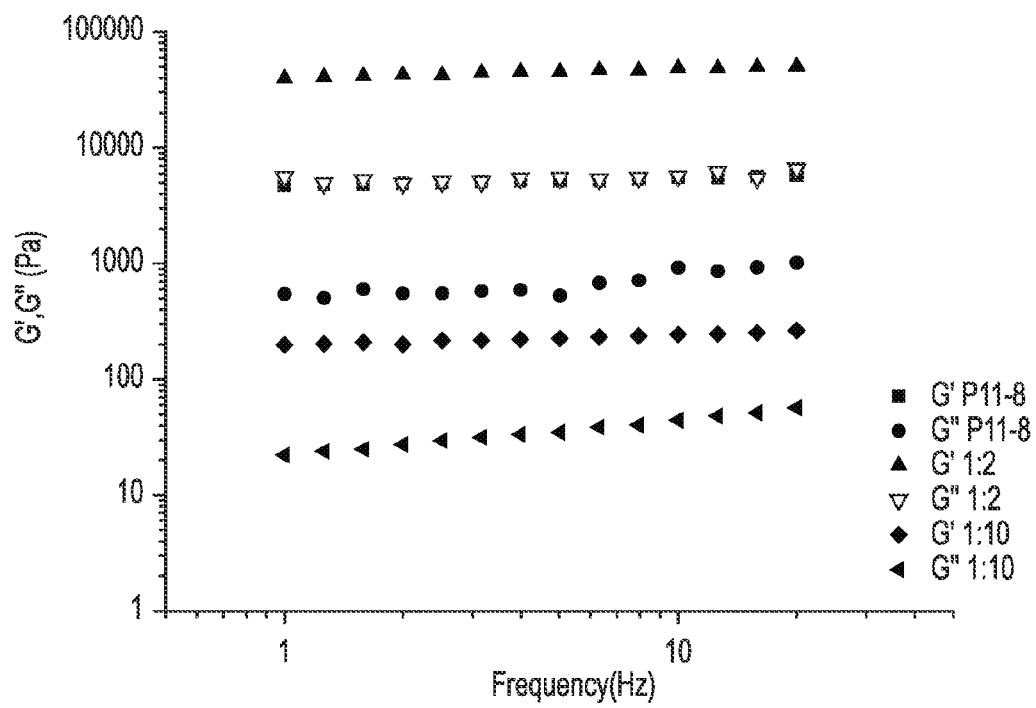
FIG. 8 shows a plot of frequency sweeps for the P11-8 peptide on its own and when mixed with two different GAG ratios (1:2 and 1:10).

FIG. 8 shows the frequency sweeps for the P11-8 peptide on its own and when mixed with two different GAG ratios.

P11-9:

From the rheometry carried out on P11-9, a strain value of 0.5% was chosen to carry out the frequency sweeps. For the 1:2 sample, the frequency sweep was carried out on the gel part of the sample, however, there may have still have been some heterogeneity to the sample. The frequency sweeps were compared to that of the P11-9 control. For all samples, the elastic modulus was higher than the viscous modulus, therefore the samples had more solid-like than liquid-like behaviour, except for the 1:2 sample. In the case of the 1:2 sample, the two moduli were very similar: This may be due to the inhomogeneous sample and so it is difficult to draw any true conclusions about its behaviour. By adding a small amount of GAG (1:0.5) to the sample, the modulus of the material was not significantly changed from the control. This was also the case for the 1:2 sample, however from the visual observations alone it was clear that the material properties of the gel had changed. By adding a larger amount of GAG (1:10) to P11-9, both the elastic and viscous moduli increased suggesting a much stiffer gel. The elastic component increased by around 50 times suggesting a much higher density of junction points. The bundles captured in the TEM study that form in the higher GAG samples may act as such junction points. The shape of the plot of the 1:10 sample is typical of that of a gel (i.e. moduli independent of frequency), whereas the other samples are typical of that of a viscoelastic solid (i.e. viscous modulus increases with frequency). This was also confirmed by the phase angle measurements, where for 1:10 the angle was unaffected by frequency and remained at around 6.3°, whereas the 1:0.5 and 1:2 phase angles increased with frequency from 3-14° and 31-40° respectively. It was observed through polarised lenses that an addition of a small concentration of GAG led to the birefringence of the gel increasing.

P11-12:

It was observed that, after the rheological experiment was carried out on the 1:0.5, 1:2, and 1:100 samples, the top cone of the rheometer could not be easily separated from the sample upon unloading. This suggests a sample with a strong molecular structure that is hard to pull apart. Amplitude sweeps were carried out to determine the linear viscoelastic region (LVER) for the 1:2 sample. From these a strain value of 0.1% was chosen for the 1:2 sample, 0.05% for the 1:10 sample, and 0.15% for the 1:100 sample for the frequency sweeps. For the 1:0.5 sample, the strain value of 0.25%, deduced for P11-12, was used for the frequency sweep. The 1:0.5, 1:2 and 1:10 samples had similar shaped plots and so are considered first. In all cases, as with the P11-12 control, the elastic modulus was higher than the viscous modulus suggesting more solid-like than liquid-like behaviour. The shape of the plots showed gel-like behaviour over the frequency range studied and this was confirmed by the phase angles being unaffected by the frequency (1:0.5=6.8°, 1:2=7.4° and 1:10=8°). The increase in the phase angle and decrease in elastic modulus as the amount of GAG is increased suggests that gels become weaker with increasing GAG ratios. It was observed that the 1:2 gel had a very slow relaxation time, even after 10 months the gel in a sample vial had not relaxed from the position it was left in after some of the gel was removed from the vial for testing. The 1:100 sample frequency sweep was very different to the others. At low frequencies, the gel was more solid-like, whereas at high frequencies it was more liquid-like. However, from looking at the combined moduli, the stiffness of the gel increased with frequency. In comparison to the other samples this sample also had a very high phase angle that increased from 39° to 55° over the frequency range, suggesting more liquid-like behaviour. The shape of the plot and the increasing phase angle was classic viscoelastic solid behaviour. It was observed when loading onto the rheometer that the gel appeared to be very elastic and not brittle at all, it was also very sticky and resisted removal from the spatula being used for loading. The top cone of the rheometer also did not easily separate from the sample on-loading and upon cleaning the surfaces seemed to be greasy.

FIG. 9 summaries the elastic and viscous modulus at 2 Hz (walking frequency) for the peptides alone and in the presence of GAG.

EXAMPLE 6

Summary of all peptide:GAG data is shown in Table 3.

| Peptide | c* (μM) | c*$_{gel}$ (μM) | GAG ratio | Time to gel 20 mg/ml | Gel lifetime 20 mg/ml | G' at 2 Hz 20 mg/ml | G" at 2 Hz 20 mg/ml | Trigger | Gel appearance |
|---|---|---|---|---|---|---|---|---|---|
| P11-4 | 310 ± 140 | 2000 ± 600 | 1:0 | mins-hours | >1 mth | 1,065 Pa | 205 Pa | pH | Slightly cloudy self-supporting gel |
| P11-4 | | | 1:2 | secs-mins | >20 days | 55 Pa | 9 Pa | GAG addition | Cloudy self-supporting gel |
| P11-4 | ~75 | | 1:10 | seconds | >20 days | 3,105 Pa | 551 Pa | GAG addition | Cloudy white self-supporting gel |
| P11-9 | 1160 ± 175 | 4500 ± 1500 | 1:0 | minutes | >1 yr 4 mths | 8 Pa | 5 Pa | pH | Clear self-supporting gel |
| P11-9 | | | 1:2 | seconds | >1 yr 4 mths | 8 Pa | 5 Pa | GAG addition | Cloudy self-supporting gel |
| P11-9 | ~1300 | | 1:10 | Seconds | >1 yr 4 mths | 366 Pa | 33 Pa | GAG addition | Cloudy self-supporting gel |
| P11-12 | 2300 ± 750 | 2300 ± 750 | 1:0 | minutes | >1 yr 11 mths | 20,510 Pa | 3067 Pa | pH | Cloudy self-supporting gel |
| P11-12 | | | 1:0.5 | minutes | >1 yr 5 mths | 21,600 Pa | 2,626 Pa | Same as control | Slightly cloudy self-supporting gel |
| P11-12 | | | 1:2 | seconds | >1 yr 5 mths | 13,960 Pa | 1,895 Pa | GAG addition | Cloudy Inhomogenous gel |
| P11-12 | ~500 | | 1:10 | seconds | >4 mths | 11,320 Pa | 1,407 Pa | GAG addition | Cloudy self-supporting gel |
| P11-12 | | | 1:20 | spontaneous | >6.5 mths | — | — | GAG addition | Cloudy self-supporting gel |
| P11-12 | | | 1:50 | spontaneous | >6.5 mths | — | — | GAG addition | Cloudy self-supporting gel |
| P11-12 | | | 1:100 | spontaneous | >6.5 mths | 2,471 Pa | 2,435 Pa | GAG addition | Cloudy self-supporting gel |
| P11-8 | 400 ± 100 | 2000 ± 600 | 1:0 | days | Still some self-supporting gel at 90 days but also liquid phase | 4,881 Pa | 552 Pa | pH | Inhomogenous cloudy self-supporting gel with some liquid phase |
| P11-8 | | | 1:2 | seconds | >90 days | 42,350 Pa | 4,931 Pa | GAG addition | Cloudy self-supporting gel slightly inhomogeneous |
| P11-8 | ~100 | | 1:10 | seconds | >90 days | 201 Pa | 28 Pa | GAG addition | Cloudy self-supporting gel |
| P11-14 | >3600 | | 1:0 | never | — | — | — | | Clear liquid |
| P11-14 | | | 1:1 | seconds | — | — | — | GAG addition | clear self-supporting gel |
| P11-14 | ~3000 | | 1:10 | spontaneous | — | — | — | GAG addition | Cloudy self-supporting gel |
| P11-28 | >3100 | | 1:0 | never | — | — | — | | Clear liquid |
| P11-28 | ~2000 | | 1:10 | | — | — | — | GAG addition | Slightly cloudy viscous liquid |
| P11-28 | | | 1:100 | minutes | — | — | — | GAG addition | Yellow self-supporting gel |

EXAMPLE 7

A bovine caudal model was used and GAG only and peptide:GAG injections were carried out into a denucleated disc. The peptide P11-12 when injected with GAG at a ratio of 1:10 significantly minimised the leakage of GAG from the disc, suggesting that the peptide was interacting with the GAG chains in such a way as to hold it in situ. This is deemed to be highly important as it is the presence of the GAG chains that should restore the disc swelling pressure and osmotic pumping action of the natural tissue, which together with the mechanical properties and volume filling action of the peptide component of the gel should help to restore the disc.

When looking into the effect of a higher GAG ratio, two different processing methods were used, with the dry powder method, the presence of P11-12 had little to no effect on a high GAG concentration. This could be due to only a certain amount of GAG being able to interact with the p11-12 aggregates and this may be at its optimum below a ratio of 1:100. Another possibility is that the processing method did not allow the GAG and the P11-12 to fully mix within the disc cavity (Data not shown).

By preparing the 1:100 GAG only and P11-12:GAG gels first and then adding to the disc, again the presence of P11-12 appears to have little effect on the overall GAG leakage when compared to that of the a GAG only gel (data not shown). This suggests that there is an optimum ratio and that there was simply too high a level of GAG in this sample for the P11-12 aggregates to interact with. However, it can be seen that this processing method leads to a reduced GAG leakage across both samples showing how important it is that the gel has mixed properly in situ. As three different trials were carried out, there were three batches of disc that had no GAG added. An interesting observation is that the variation in natural GAG leakage over six different tails was also checked and no significant difference was observed between any of the three trials in the natural leakage. This is a positive result, because six different tails were used that could have had different degeneration/healthy states, which would have been dependent on many external factors.

Figure 10:
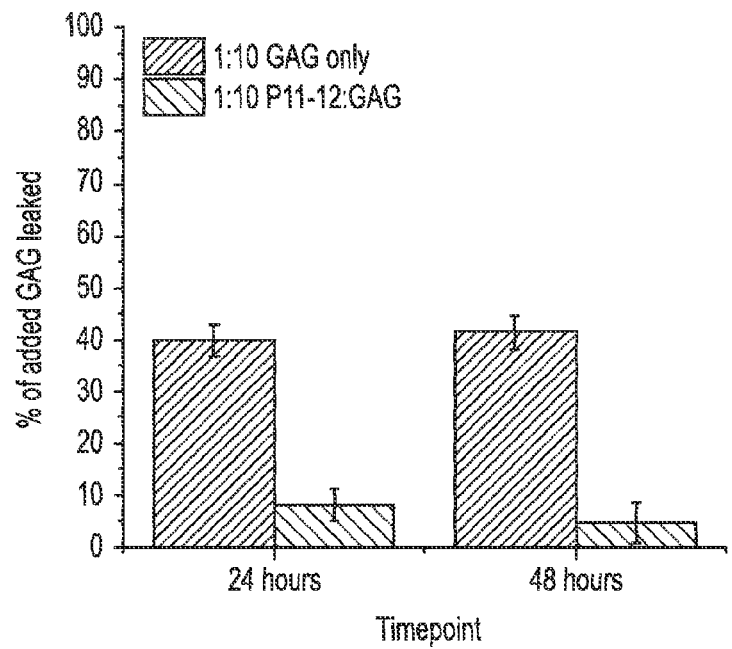
FIG. 10 shows a comparison of percentage of added GAG leaked (GAG concentration−natural leakage) from a disc over a 48 hr time period when injected with 1:10 GAG only and 1:10 P11-12:GAG.

Discs were placed in PBS for 48 hours and the amount of GAG leakage was monitored at 2 time-points by a DMMB assay. FIG. 10 shows a comparison of percentage of added GAG leaked (GAG concentration-natural leakage) from a disc over a 48 hr time period when injected with 1:10 GAG only and 1:10 P11-12:GAG. It was found that the presence of P11-12 significantly reduced the loss of GAG from the disc and suggests that gelation and self-assembly were successful within the disc and that the P11-12 aggregates were interacting with the GAG chains binding them in place.

EXAMPLE 8

Experiments were conducted to assess how these new peptide:GAG hybrid gels compared to the natural tissue, in order to assess their behaviour a compressive loading experiment was undertaken. As a first step the disc nucleated, denucleated and denucleated plus peptide:GAG gels were tested under static loading and the resultant load displacement curves were plotted (data not shown).

Static axial loading was carried out using a materials testing rig and from the load displacement plots normalised stiffness values were compared for a denucleuated disc, nucleated disc and denucleated and then repaired with peptide:GAG. The denucleated model used here allowed the AF to relax into the nucleus cavity prior to testing. This resembles the degenerated state where the NP loses fluid and becomes more fibrous. It should be noted that this model is therefore stiffer than the model with the natural nucleus intact, which is in contrast to other denucleated models reported in literature.

A comparison of the load-displacement curves, showed that there are some trends visible in the shapes and positions of the curves. The denucleated samples suggested that they do not deform as much for a given load in comparison to the samples with the nucleus intact. The samples that had their nucleus replaced with P11-12:GAG gels fall somewhere between the two suggesting the gel is at least somewhat restoring the biomechanics of the disc.

From the load-displacement plots, the normalised stiffness values for each group were calculated. The two control groups (No NP and NP) were significantly different from one another. The 1:2 sample showed no significant difference to the disc with the natural nucleus intact and was significantly different to the denucleated disc; however the 1:10 sample showed the opposite behaviour. From the rheology investigation carried out the p11-12:GAG 1:2 gel was expected to restore the most similar biomechanics to the natural tissue as it had the most similar elastic modulus to that of the unconfined nucleus pulposus.

Figure 11:
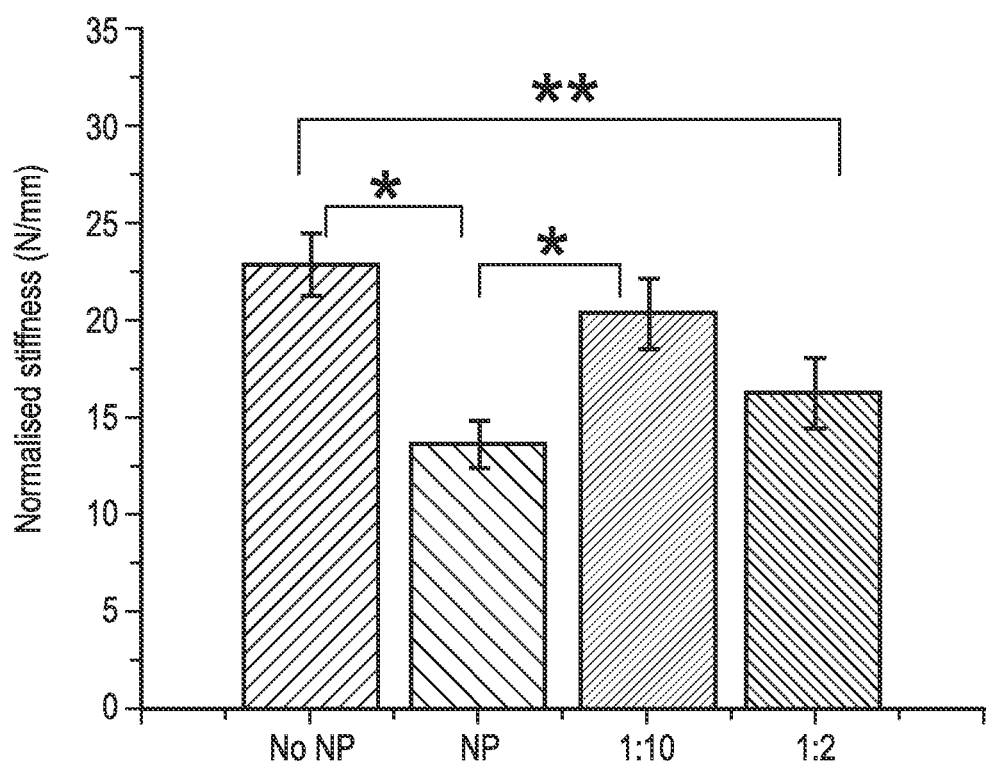
FIG. 11 shows a plot of normalised stiffness for each sample type as an average of the six discs tested.

Although no significant difference is seen between the denucleated discs and the disc containing P11-12:GAG 1:10, from observing the general trends it is clear that replacement of the nucleus with a P11-12:GAG gel improves the stiffness to a value closer to that of the natural tissue. FIG. 11 shows a plot of normalised stiffness for each sample type as an average of the six discs tested and data demonstrates that repaired disc stiffness is restored to that of a healthy disc.

The observations seen here can be explained by how the compressive load is distributed by the tissue. When loading the intact nucleus, the fluid part of the tissue is pressurised, causing the AF to bulge outwards, whereas when loading the denucleated samples, only the solid phase of the tissue is loaded and the AF bulges into the denucleated cavity. Also when the discs are denucleated, it is likely that there is a relaxation of the AF and a reduction in height of the disc even before load is applied. Therefore the AF has already been slightly compressed and so is stiffer than in the intact case. Effectively, the discs are starting from a different position. The repaired samples fall somewhere between the intact and denucleated nuclei, which is thought to be due to two reasons. Firstly, because the AF has bulged slightly into the nucleated cavity prior to injection and loading, the load is carried partly by the solid phase of the AF and partly by the fluid phase of the hydrogel, secondly, because the disc height will have been altered during the denuclation process prior to injection, this will again result in a different starting position.

The invention claimed is:

1. A composition of matter comprising a self-assembling peptide complex, the complex comprising:
   (i) at least one charged self-assembling peptide, the peptide comprising 11 amino acid residues and comprising a hydrophobic aromatic core, wherein the amino acids at positions 4 and 8 are phenylalanine (F) and the amino acid at position 6 is tryptophan (W); and
   (ii) an oppositely or same charged polysaccharide, wherein the peptide and polysaccharide are not covalently bonded together, and wherein the peptide and/or self-assembling peptide complex forms ribbons, fibrils, fibers or a three dimensional scaffold in a β-sheet tape-like substructure.

2. The composition according to claim 1, wherein the self-assembling peptide is selected from the group consisting of P11-12 (SEQ ID NO:2), P11-8 (SEQ ID NO:1), P11-14 (SEQ ID NO: 3), P11-16 (SEQ ID NO: 4), P11-18 (SEQ ID NO:5), P11-28 (SEQ ID NO:8), P11-31 (SEQ ID NO:9), P11-32 (SEQ ID NO:10), P11-4 (SEQ ID NO:11), P11-9 (SEQ ID NO:12), P11-13 (SEQ ID NO:13), P11-15 (SEQ ID NO:14), P11-17 (SEQ ID NO:15), P11-29 (SEQ ID NO:20) and P11-30 (SEQ ID NO:21).

3. The composition according to claim 1 wherein the overall net charge on the peptide is +/−2, +/−4 or +/−6.

4. The composition of claim 1, wherein:
   the amino acid residues at both positions 5 and 7 of the peptide is ornithine (O) or glutamic acid (E); and
   the amino acid residues at positions 1 and 2 on the peptide are the same or different but reversed at positions 10 and 11.

5. The composition according to claim 1, wherein the self-assembling peptide is a positively charged peptide and is associated with a polysaccharide selected from the group consisting of glycosaminoglycan (GAG), oligosaccharide, mucopolysaccharide and dextran.

6. The composition according to claim 5, wherein the polysaccharide is negatively charged and is a glycosaminoglycan (GAG) selected from the group consisting of chondroitin sulfate, dermatan sulfate, kertatan sulfate, hyaluronan, hyaluronic acid, heparin and heparan sulphate.

7. The composition according to claim 1, wherein the self-assembling peptide complex is P11-12 (SEQ ID NO: 2): GAG, P11-8 (SEQ ID NO: 1): GAG, P11-14 (SEQ ID NO: 3): GAG, P11-16 (SEQ ID NO: 4): GAG, P11-18 (SEQ ID NO: 5): GAG, P11-28 (SEQ ID NO: 8) GAG, P11-31 (SEQ ID NO: 9): GAG, P11-32 (SEQ ID NO:10): GAG, P11-4 (SEQ ID NO:11):GAG, P11-9 (SEQ ID NO:12):GAG, P11-13 (SEQ ID NO:13):GAG, P11-15 (SEQ ID NO:14):GAG, P11-17 (SEQ ID NO:15):GAG, P1129 (SEQ ID NO:20): GAG or P11-30 (SEQ ID NO:21):GAG.

8. The composition according to claim 1, wherein the self-assembling peptide is a positively charged peptide and is associated with a positively charged polysaccharide selected from the group consisting of chitosan and its derivatives and other cationic polysaccharides.

9. The composition according to claim 1, wherein the self assembling peptide is negatively charged and is associated with a negatively charged polysaccharide selected from the group consisting of glycosaminoglycan (GAG), oligosaccharide, mucopolysaccharide and dextran.

10. The composition according to claim 9, wherein the negatively charged polysaccharide is a glycosaminoglycan (GAG) selected from the group consisting of chondroitin sulfate, dermatan sulfate, kertatan sulfate, hyaluronan, hyaluronic acid, heparin and heparan sulphate.

11. The composition according to claim 1, wherein the self-assembling peptide is negatively charged and is associated with a positively charged polysaccharide selected from the group consisting of chitosan and its derivatives and other cationic polysaccharides.

12. The composition of claim 1 wherein the self-assembling peptide complex has an elastic modulus in the range 1 to 400,000 Pa.

13. The composition according to claim 1, wherein the self-assembling peptide complex is in a gel, fluid, semi-solid, hydrogel, viscous solution, Newtonian fluid solution, aerogel, visco-elastic solid, xerogel, surface coating, film or a non-woven fabric.

14. The self-assembling peptide complex of claim 1, further comprising a bioactive peptide sequence attached on either or both of the peptide termini.

15. A kit comprising:
   (i) an injectable charged polysaccharide, and
   at least one injectable self-assembling peptide selected from the group comprising wherein the self-assembling peptide is selected from the group consisting of P11-12 (SEQ ID NO:2), P11-8 (SEQ ID NO:1), P11-14 (SEQ ID NO: 3), P11-16 (SEQ ID NO: 4), P11-18 (SEQ ID NO:5), P11-28 (SEQ ID NO:8), P11-31 (SEQ ID NO:9), P11-32 (SEQ ID NO: 10), P11-4 (SEQ ID NO:11), P11-9 (SEQ ID NO:12), P11-13 (SEQ ID NO:13), P11-15 (SEQ ID NO:14), P11-17 (SEQ ID NO:15), P11-29 (SEQ ID NO:20) and P11-30 (SEQ ID NO:21);
   wherein upon injection of the polysaccharide and the peptide a peptide complex is formed that has an elastic modulus in the range 1 to 400,000 Pa, the kit optionally further including a set of written instructions.

16. The kit according to claim 15, further comprising a syringe comprising two barrels, wherein a first barrel comprises the polysaccharide and a second barrel comprises the peptide and the first and the second barrels are adapted to be in fluid communication when the peptide and polysaccharide are ejected from the syringe to allow mixing of the peptide and polysaccharide.

17. A method of preparing a self-assembling peptide complex, comprising:
   mixing the composition of claim 1 with a negatively charged polysaccharide in a selected ratio so as to form a gel.

18. The method according to claim 17, wherein the composition is present in a saline solution.

19. The method according to claim 17, wherein mixing the charged self-assembling peptide and the polysaccharide comprises simultaneous injection into a recipient directly to the point at which it is desired to form a gel in situ.

20. The method according to claim 17, wherein mixing the charged self-assembling peptide comprises injection to an appropriate site before or after injection of the polysaccharide.

21. An injectable biomaterial composition comprising a self-assembling peptide complex, the complex comprising:
   (i) at least one charged self-assembling peptide comprising 11 amino acids residues and having a hydrophobic aromatic core wherein the amino acid at positions 4 and 8 are phenylalanine (F) and the amino acid at position 6 is tryptophan (W); and
   ii) an oppositely or same charged polysaccharide, wherein the peptide and polysaccharide are not covalently bonded together, and wherein the peptide and/or self-assembling peptide complex forms ribbons, fibrils, fibers or a three dimensional scaffold in a β-sheet tape-like substructure.

22. The biomaterial composition according to claim 21, wherein the composition forms a gel, semi-solid, hydrogel, viscous solution, visco-elastic solid, xerogel, surface coating or film at the site where it has been injected.

23. A personal care product, tissue reconstruction device, scaffold for tissue engineering or an adjunct for ophthalmology procedures comprising the self-assembling peptide complex of claim 1.

24. A method of repairing or replacing or restoring the nucleus pulposus of a disc, comprising administering the self-assembling peptide complex according to claim 1 into an area of the nucleus pulposus of a disc that requires treatment.

25. The method according to claim 24, wherein the self-assembling peptide complex has shear elastic and viscous moduli in the range of 8-12 kPa for G' and 3.5 to 5.5 kPa for G".

* * * * *

SEQUENCE LISTING

```
<160> NUMBER OF SEQ ID NOS: 21

<210> SEQ ID NO 1
<211> LENGTH: 11
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 1

Gln Gln Arg Phe Xaa Trp Xaa Phe Glu Gln Gln
1               5                   10
```

```
<210> SEQ ID NO 2
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 2

Ser Ser Arg Phe Xaa Trp Xaa Phe Glu Ser Ser
1               5                   10

<210> SEQ ID NO 3
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 3

Gln Gln Xaa Phe Xaa Trp Xaa Phe Xaa Gln Gln
1               5                   10

<210> SEQ ID NO 4
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 4

Asn Asn Arg Phe Xaa Trp Xaa Phe Glu Asn Asn
1               5                   10

<210> SEQ ID NO 5
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
```

```
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 5

Thr Thr Arg Phe Xaa Trp Xaa Phe Glu Thr Thr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 6

Gln Gln Arg Gln Xaa Gln Xaa Gln Glu Gln Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 7

Gln Gln Xaa Gln Xaa Gln Xaa Gln Xaa Gln Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (3)..(3)
<223> OTHER INFORMATION: Orn
<220> FEATURE:
```

```
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn
<220> FEATURE:
<221> NAME/KEY: MOD_RES
<222> LOCATION: (11)..(11)
<223> OTHER INFORMATION: Orn

<400> SEQUENCE: 8

Xaa Gln Xaa Phe Xaa Trp Xaa Phe Xaa Gln Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 9

Ser Ser Xaa Phe Xaa Trp Xaa Phe Xaa Ser Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn
<220> FEATURE:
<221> NAME/KEY: MOD_RES
```

```
<222> LOCATION: (11)..(11)
<223> OTHER INFORMATION: Orn

<400> SEQUENCE: 10

Xaa Ser Xaa Phe Xaa Trp Xaa Phe Xaa Ser Xaa
1               5                   10

<210> SEQ ID NO 11
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 11

Gln Gln Arg Phe Glu Trp Glu Phe Glu Gln Gln
1               5                   10

<210> SEQ ID NO 12
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 12

Ser Ser Arg Phe Glu Trp Glu Phe Glu Ser Ser
1               5                   10

<210> SEQ ID NO 13
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 13

Glu Gln Glu Phe Glu Trp Glu Phe Glu Gln Glu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 14

Asn Asn Arg Phe Glu Trp Glu Phe Glu Asn Asn
1               5                   10

<210> SEQ ID NO 15
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 15

Thr Thr Arg Phe Glu Trp Glu Phe Glu Thr Thr
1               5                   10

<210> SEQ ID NO 16
<211> LENGTH: 11
<212> TYPE: PRT
<213> ORGANISM: Artificial Sequence
<220> FEATURE:
```

<223> OTHER INFORMATION: SYNTHETIC PEPTIDE

<400> SEQUENCE: 16

Gln Gln Arg Gln Glu Gln Glu Gln Glu Gln Gln
1               5                   10

<210> SEQ ID NO 17
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 17

Ser Ser Arg Gln Glu Gln Glu Gln Glu Ser Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 18

Ser Ser Arg Ser Glu Ser Glu Ser Glu Ser Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 19

Glu Gln Glu Gln Glu Gln Glu Gln Glu Gln Glu
1               5                   10

<210> SEQ ID NO 20
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 20

Gln Gln Glu Phe Glu Trp Glu Phe Glu Gln Gln
1               5                   10

<210> SEQ ID NO 21
<211> LENGTH: 11
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: misc_feature
<223> OTHER INFORMATION: X is ornithine
<220> FEATURE:
<221> NAME/KEY: misc_feature
<222> LOCATION: (1)..(11)
<223> OTHER INFORMATION: X is ornithine

<400> SEQUENCE: 21

Glu Ser Glu Phe Glu Trp Glu Phe Glu Ser Glu
1               5                   10